United States Patent
Bachmann et al.

(10) Patent No.: US 10,047,225 B2
(45) Date of Patent: Aug. 14, 2018

(54) STYRYL SULFIDE DYES

(71) Applicant: BASF SE, Ludwigshafen (DE)

(72) Inventors: Frank Bachmann, Freiburg (DE);
Christian Cremer, Lörrach (DE);
Markus Knobloch, Müllheim (DE);
Beate Fröhling, Neustadt (DE);
Werner Specker, Lörrach (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 14/915,447

(22) PCT Filed: Aug. 28, 2014

(86) PCT No.: PCT/EP2014/068242
§ 371 (c)(1),
(2) Date: Feb. 29, 2016

(87) PCT Pub. No.: WO2015/028543
PCT Pub. Date: Mar. 5, 2015

(65) Prior Publication Data
US 2016/0208103 A1    Jul. 21, 2016

(30) Foreign Application Priority Data
Sep. 2, 2013    (EP) .................... 13182635

(51) Int. Cl.
*C09B 23/14*    (2006.01)
*A61K 8/49*    (2006.01)
(Continued)

(52) U.S. Cl.
CPC .......... *C09B 23/145* (2013.01); *A61K 8/4926* (2013.01); *A61Q 5/10* (2013.01); *C07D 213/56* (2013.01); *C07D 401/14* (2013.01)

(58) Field of Classification Search
CPC .................................... C09B 23/145
(Continued)

(56) References Cited

U.S. PATENT DOCUMENTS 3,369,970 A    2/1968  McLaughlin et al.
4,786,493 A    11/1988 Smith et al.
(Continued)

FOREIGN PATENT DOCUMENTS

CA    2288055 A1    10/1998
CA    2277347 A1    1/2000
(Continued)

OTHER PUBLICATIONS

Miller et al., J. Chromatography A, vol. 865 (1999) pp. 211-226.*
(Continued)

*Primary Examiner* — Taofiq A Solola
(74) *Attorney, Agent, or Firm* — Drinker Biddle & Reath LLP

(57) ABSTRACT

Disclosed are styryl dyes of formula

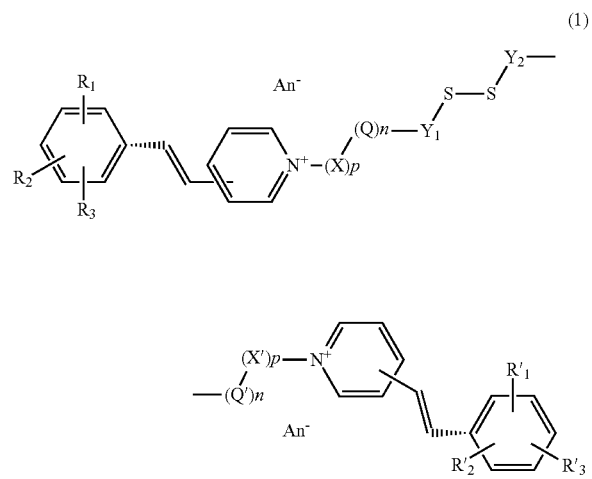

(1)

wherein
$R_1$, $R_2$, $R_3$, $R'_1$, $R'_2$ and $R'_3$ independently of each other are hydrogen; —NH(CO)—$C_1$-$C_5$alkyl; —N($C_1$-$C_5$alkyl)($C_1$-$C_5$alkyl-CN); $C_1$-$C_6$alkoxy; a heterocyclic radical; or $R_1$ and $R_2$ or $R'_1$ and $R'_2$ together form a 5- to 10-membered, monocyclic, carbocyclic or heterocyclic ring; wherein at least one of $R_1$, $R_2$, $R_3$, $R'_1$, $R'_2$ and $R'_3$ is different from hydrogen;
Q and Q' independently from each other are the direct bond; *—C(O)—*; *—C(O)O—*; *—OCO—*; *—N($R_4$)—*;

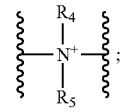

*—C(O)N($R_6$)—*; or *—($R_6$)NC(O)—*; and
$R_4$, $R_5$ and $R_6$ independently from each other are hydrogen; $C_1$-$C_{14}$alkyl; $C_2$-$C_{14}$alkenyl; $C_6$-$C_{12}$aryl; $C_6$-$C_{12}$aryl-$C_1$-$C_{10}$alkyl; or $C_1$-$C_{10}$alkyl($C_5$-$C_{12}$aryl);
X and X' are *—$(CH_2)_m$—*;
$Y_1$ and $Y_2$ independently from each other are $C_1$-$C_{10}$alkylene; $C_5$-$C_{10}$cycloalkylene; $C_5$-$C_{12}$arylene; or $C_5$-$C_{12}$arylene-($C_1$-$C_{10}$alkylene);
An⁻ is an anion;
m is a number from 1 to 8;
n is 0, or 1; and
p is 0, or 1.

1 Claim, No Drawings

(51) Int. Cl.
 *A61Q 5/10* (2006.01)
 *C07D 213/56* (2006.01)
 *C07D 401/14* (2006.01)

(58) Field of Classification Search
 USPC .................................................. 546/256
 See application file for complete search history.

(56) References Cited

U.S. PATENT DOCUMENTS

| | | |
|---|---|---|
| 4,865,774 A | 9/1989 | Fabry et al. |
| 4,931,218 A | 6/1990 | Schenker et al. |
| 5,135,543 A | 8/1992 | Chan et al. |
| 5,169,403 A | 12/1992 | Chan et al. |
| 5,256,823 A | 10/1993 | Chan et al. |
| 5,294,726 A | 3/1994 | Behler et al. |
| 5,298,029 A | 3/1994 | Chan et al. |
| 5,360,930 A | 11/1994 | Chan et al. |
| 5,486,629 A | 1/1996 | Chan et al. |
| 5,708,151 A | 1/1998 | Möckli |
| 5,830,441 A | 11/1998 | Wang et al. |
| 5,919,273 A | 7/1999 | Rondeau et al. |
| 5,922,310 A | 7/1999 | Chaudhuri et al. |
| 5,993,490 A | 11/1999 | Rondeau et al. |
| 6,001,135 A | 12/1999 | Rondeau et al. |
| 6,190,421 B1 | 2/2001 | Rondeau et al. |
| 6,228,129 B1 | 5/2001 | de la Mettrie et al. |
| 6,248,314 B1 | 6/2001 | Nakashimada et al. |
| 6,368,360 B2 | 4/2002 | Samain |
| 6,419,711 B1 | 7/2002 | Genet et al. |
| 6,432,146 B1 | 8/2002 | Rondeau |
| 6,436,153 B2 | 8/2002 | Rondeau |
| 6,503,283 B1 | 1/2003 | Lang et al. |
| 6,530,959 B1 | 3/2003 | Lang et al. |
| 6,660,046 B1 | 12/2003 | Terranova et al. |
| 6,712,861 B2 | 3/2004 | Rondeau |
| 6,843,256 B2 | 1/2005 | Möckli |
| 6,863,883 B1 | 3/2005 | Tsujino et al. |
| 7,087,096 B2 | 8/2006 | Rondeau |
| 7,476,260 B2 | 1/2009 | Eliu et al. |
| 7,485,157 B2 | 2/2009 | Rondeau |
| 7,507,260 B2 | 3/2009 | Rondeau et al. |
| 7,550,016 B2 | 6/2009 | Cremer et al. |
| 7,563,289 B2 | 7/2009 | Eliu et al. |
| 7,686,850 B2 | 3/2010 | Cremer et al. |
| 7,704,284 B2 | 4/2010 | Eliu et al. |
| 7,731,760 B2 | 6/2010 | Cremer et al. |
| 7,771,490 B2 | 8/2010 | Eliu et al. |
| 7,785,375 B2 | 8/2010 | Eliu et al. |
| 7,789,916 B2 | 9/2010 | Cremer et al. |
| 7,806,940 B2 | 10/2010 | Eliu et al. |
| 7,811,335 B2 | 10/2010 | Eliu et al. |
| 7,828,858 B2 | 11/2010 | Cremer et al. |
| 7,931,696 B2 | 4/2011 | Eliu et al. |
| 8,641,783 B2 | 2/2014 | Marquais-Bienewald et al. |
| 8,992,633 B2 | 3/2015 | Marquais-Bienewald et al. |
| 2005/0235433 A1 | 10/2005 | Rondeau |
| 2006/0070191 A1 | 4/2006 | Lang et al. |
| 2009/0172897 A1 | 7/2009 | Daubresse et al. |
| 2011/0011417 A1 | 1/2011 | Greaves et al. |
| 2013/0074276 A1 | 3/2013 | Daubresse et al. |

FOREIGN PATENT DOCUMENTS

| | | |
|---|---|---|
| CA | 2288253 A1 | 5/2000 |
| DE | 3 723 354 A1 | 1/1989 |
| DE | 3 725 030 A1 | 2/1989 |
| DE | 3 829 870 A1 | 4/1989 |
| DE | 3 926 344 A1 | 2/1991 |
| DE | 4 421 031 A1 | 12/1995 |
| DE | 19 713 698 C1 | 6/1998 |
| DE | 19 717 224 A1 | 10/1998 |
| DE | 19 729 080 C1 | 11/1998 |
| DE | 299 12 327 U1 | 10/1999 |
| DE | 19 959 479 A1 | 7/2001 |
| EP | 312 343 A2 | 4/1989 |
| EP | 404 868 A1 | 1/1991 |
| EP | 714954 A2 | 6/1996 |
| EP | 758 547 A1 | 2/1997 |
| EP | 801 942 A1 | 10/1997 |
| EP | 818 193 A2 | 1/1998 |
| EP | 834 303 A2 | 4/1998 |
| EP | 850 636 A1 | 7/1998 |
| EP | 850 637 A1 | 7/1998 |
| EP | 850 638 A1 | 7/1998 |
| EP | 953 334 A2 | 11/1999 |
| EP | 962 219 A2 | 12/1999 |
| EP | 970 685 A1 | 1/2000 |
| EP | 970 687 A1 | 1/2000 |
| EP | 998908 A2 | 5/2000 |
| EP | 1062940 A1 | 12/2000 |
| EP | 1 166 752 A2 | 1/2002 |
| FR | 2788432 A1 | 7/2000 |
| GB | 2 319 776 A | 6/1998 |
| JP | S4823911 B1 | 7/1973 |
| JP | S61210023 A | 9/1986 |
| JP | H07101841 A | 4/1995 |
| JP | H08245348 A | 9/1996 |
| JP | H09255540 A | 9/1997 |
| JP | H1053970 A | 2/1998 |
| JP | H1087450 A | 4/1998 |
| WO | WO-9001922 A1 | 3/1990 |
| WO | WO-95/01772 A1 | 1/1995 |
| WO | WO-97/20545 A1 | 6/1997 |
| WO | WO-98/22447 A1 | 5/1998 |
| WO | WO-99/20234 A1 | 4/1999 |
| WO | WO-99/20235 A1 | 4/1999 |
| WO | WO-99/40895 A1 | 8/1999 |
| WO | WO-99/48856 A1 | 9/1999 |
| WO | WO-00/10517 A1 | 3/2000 |
| WO | WO-00/10518 A1 | 3/2000 |
| WO | WO-00/10519 A1 | 3/2000 |
| WO | WO-00/12057 A1 | 3/2000 |
| WO | WO-00/28957 A1 | 5/2000 |
| WO | WO-00/43367 A1 | 7/2000 |
| WO | WO-01/36396 A1 | 5/2001 |
| WO | WO-01/66646 A1 | 9/2001 |
| WO | WO-02/31056 A1 | 4/2002 |
| WO | WO-2004/019897 A1 | 3/2004 |
| WO | WO-2007/003506 A1 | 1/2007 |
| WO | WO-2007110539 A2 | 10/2007 |
| WO | WO-2007110540 A2 | 10/2007 |
| WO | WO-2007110541 A2 | 10/2007 |
| WO | WO-2012113722 A2 | 8/2012 |

OTHER PUBLICATIONS

Karrer, Org. Chem. 2nd Ed. (1946), Elsevier Publishing Co., Inc. NY., 1946, pp. 91-102.*

International Search Report for PCT/EP2014/068242 mailed Dec. 4, 2014.

Asquith et al., "Communications the Reactions of Disulphide Dyes for the Covalent Coloration of Keratin", JSDC, pp. 168-172, May 1973.

* cited by examiner

STYRYL SULFIDE DYES

CROSS-REFERENCE TO RELATED APPLICATIONS

This application is a national stage application (under 35 U.S.C. § 371) of PCT/EP2014/068242, filed Aug. 28, 2014, which claims benefit of European Application No. 13182635.6, filed Sep. 2, 2013, both of which are incorporated herein by reference in their entirety.

The present invention relates to novel styryl sulfide dyes and the preparation of these compounds.

It is known, for example, from WO 95/01772 that cationic dyes can be used for the dyeing of organic material, for example keratin, silk, cellulose or cellulose derivatives, and also synthetic fibers, for example polyamides. Cationic dyes exhibit very brilliant shades. A disadvantage is their unsatisfactory fastness to washing.

R. S. Asquith, P. Carthew and T. T. Francis describe in JSDC from May 1973, pages 168-172 that ortho-azo disulfide dyes do not lead to covalent bonding with keratin fiber of wool, and that para-azo disulfide dyes underwent only at high concentration some covalent bindings with wool.

The technical problem is to provide dyes that are distinguished by deep dying having good fastness properties with respect to washing, light, shampooing and rubbing.

Accordingly, the present invention relates to styryl disulfide dyes of formula

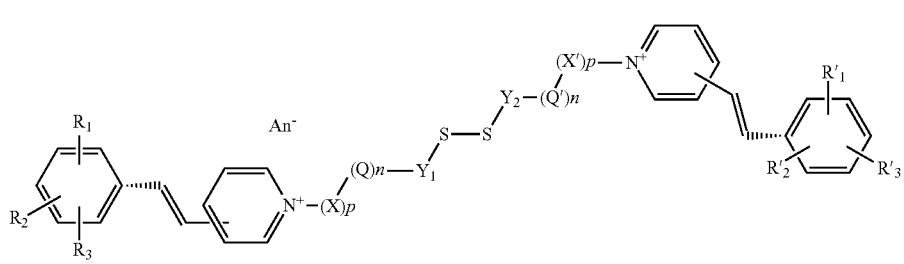

(1)

wherein $R_1$, $R_2$, $R_3$, $R'_1$, $R'_2$ and $R'_3$ independently of each other are hydrogen; —NH(CO)—$C_1$-$C_6$alkyl; —N($C_1$-$C_5$alkyl)($C_1$-$C_5$alkyl-CN); $C_1$-$C_6$alkoxy; a heterocyclic radical; or $R_1$ and $R_2$ or $R'_1$ and $R'_2$ together form a 5- to 10-membered, monocyclic, carbocyclic or heterocyclic ring; wherein at least one of $R_1$, $R_2$, $R_3$, $R'_1$, $R'_2$ and $R'_3$ is different from hydrogen;

Q and Q' independently from each other are *—C(O)—*; *—C(O)O—*; *—OCO—*;
*—N($R_4$)—*;

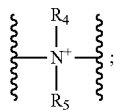

*—C(O)N($R_6$)—*; or *—($R_6$)NC(O)—*;

$R_4$, $R_5$ and $R_6$ independently from each other are hydrogen; $C_1$-$C_{14}$alkyl; $C_2$-$C_{14}$alkenyl; $C_6$-$C_{12}$aryl; $C_6$-$C_{12}$aryl-$C_1$-$C_{10}$alkyl; or $C_1$-$C_{10}$alkyl($C_5$-$C_{12}$aryl);

X and X' are *—$(CH_2)_m$—*;

$Y_1$ and $Y_2$ independently from each other are $C_1$-$C_{10}$alkylene; $C_8$-$C_{10}$cycloalkylene; $C_8$-$C_{12}$arylene; or $C_5$-$C_{12}$arylene-($C_1$-$C_{10}$alkylene);

$An^-$ is an anion;

m is a number from 1 to 8;

n is 0, or 1; and p is 0, or 1.

$C_1$-$C_{10}$alkyl are straight chain or branched alkyl radicals like methyl, ethyl, n-propyl, isopropyl, n-butyl, sec.butyl, tert.butyl, amyl, isoamyl or tert.amyl, hexyl, 2-ethylhexyl, heptyl, octyl, isooctyl, nonyl or decyl.

$C_1$-$C_6$alkoxy is for example methoxy, ethoxy, n-propoxy, isopropoxy, n-butoxy, sec.butoxy, tert.butoxy, amyloxy, isoamyloxy, tert.amyloxy or hexyloxy.

$C_5$-$C_{12}$aryl is for example naphthyl and preferably phenyl.

$C_1$-$C_{10}$alkylene is for example methylene, ethylene, propylene, isopropylene, n-butylene, secbutylene, tert-butylene, n-pentylene, 2-pentylene 3-pentylene, 2,2'-dimethylpropylene, cyclopentylene, cyclohexylene, n-hexylene, n-octylene, 1,1',3,3'-tetramethylbutylene, 2-ethylhexylene, nonylene or decylene.

$C_5$-$C_{10}$cycloalkylene is for example cyclopentylene, cycloheptylene, cyclooctylene, cyclononylene or cyclodecylene and preferably cyclohexylene.

$C_5$-$C_{12}$arylene is for example naphthylene and preferably phenylene.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formiate, acetate, propionate or a complex anion, such as the zinc chloride double salt.

The anion is especially a halide, preferably chloride or fluoride, sulfate, hydrogen sulfate, methyl sulfate, ethyl sulfate, phosphate, formiate, acetate or lactate.

The anion is more especially fluoride, chloride, methyl sulfate, ethyl sulfate, formate or acetate.

Preferred styryl sulfide dyes of formula (1) are compounds, wherein $R_1$, $R_2$, $R_3$, $R'_1$, $R'_2$ and $R'_3$ independently of each other are hydrogen; or $C_1$-$C_6$alkoxy; wherein at least one of $R_1$, $R_2$, $R_3$, $R'_1$, $R'_2$ or $R'_3$ is $C_1$-$C_6$alkoxy.

More preferred styryl sulfide dyes of formula (1) are compounds, wherein $R_1$, $R_2$, $R_3$, $R'_1$, $R'_2$ and $R'_3$ are hydrogen; or methoxy; wherein at least one of $R_1$, $R_2$, $R_3$, $R'_1$, $R'_2$ and $R'_3$ is methoxy.

Further preferred styryl sulfide dyes of formula (1) are compounds, wherein $R_1$, $R_2$, $R_3$, $R'_1$, $R'_2$ and $R'_3$ independently of each other is hydrogen; —NH(CO)—$C_1$-$C_5$alkyl; or —N($C_1$-$C_5$alkyl)($C_1$-$C_5$alkyl-CN); wherein at least one of $R_1$, $R_2$, $R_3$, $R'_1$, $R'_2$ or $R'_3$ is selected from —N($C_1$-$C_6$alkyl)($C_1$-$C_5$alkyl-CN); and —NH(CO)—$C_1$-$C_5$alkyl.

More preferred styryl sulfide dyes of formula (1) are compounds, wherein at least one of $R_1$, $R_2$, $R_3$, $R'_1$, $R'_2$ or $R'_3$ is —N(CO)—$CH_3$ or —N($CH_3$)($CH_2$)$_2$—CN, Most preferred styryl sulfide dyes are compounds of formula (1), wherein
$Y_1$ and $Y_2$ independently from each other are $C_1$-$C_{10}$alkylene.

Most preferred styryl sulfide dyes according to the present invention are those compounds of formula (1), wherein
$R_1$ is identical to $R_1'$;
$R_2$ is identical to $R_2'$;
$R_3$ is identical to $R_3'$;
X is identical to X';
Q is identical to Q'; and
$Y_1$ is identical to $Y_2$.

Most preferred styryl sulfide dyes according to the present invention correspond to formula

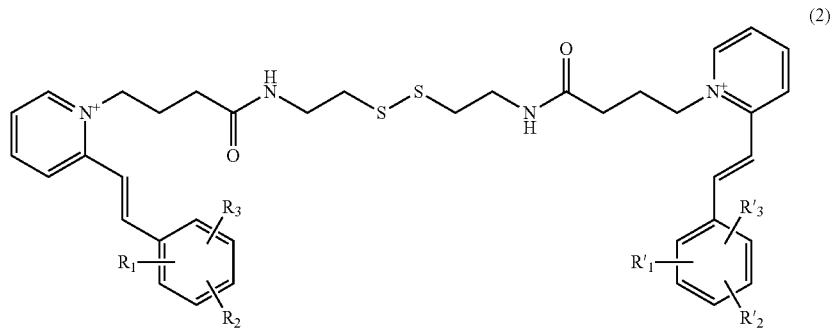

(2)

wherein
$R_1$, $R_2$, $R_3$, $R'_1$, $R'_2$ and $R'_3$ are defined as in formula (1).

Most preferred styryl sulfide dyes of formula (2) are compounds, wherein
$R_1$, $R_2$, $R_3$, $R'_1$, $R'_2$ and $R'_3$ is hydrogen; or methoxy; wherein at least one of $R_1$, $R_2$, $R_3$, $R'_1$, $R'_2$ or $R'_3$ is methoxy.

Also preferred styryl sulfide dyes of formula (2) are compounds, wherein $R_1$, $R_2$, $R_3$, $R'_1$, $R'_2$ and $R'_3$ independently of each other are hydrogen; —NH(CO)—$C_1$-$C_5$alkyl; or —N($C_1$-$C_5$alkyl)($C_1$-$C_5$alkyl-CN); wherein at least one of $R_1$, $R_2$, $R_3$, $R'_1$, $R'_2$ or $R'_3$ is —NH(CO)—$C_1$-$C_5$alkyl.

Further preferred styryl sulfide dyes according to the present invention correspond to formula wherein
$R_1$, $R_2$, $R_3$, $R'_1$, $R'_2$ and $R''_3$ and An are defined as in formula (1).

Most preferred styryl sulfide dyes of formula (3) are compounds, wherein
$R_1$, $R_2$, $R_3$, $R'_1$, $R'_2$ and $R'_3$ is hydrogen; or methoxy; wherein at least one of $R_1$, $R_2$, $R_3$, $R'_1$, $R'_2$ or $R'_3$ is methoxy.

Further preferred styryl sulfide dyes of formula (3) are compounds, wherein
$R_1$, $R_2$, $R_3$, $R'_1$, $R'_2$ and $R'_3$ independently of each other is hydrogen; or —NH(CO)—$C_1$-$C_5$alkyl; wherein at least one of $R_1$, $R_2$, $R_3$, $R'_1$, $R'_2$ or $R'_3$ is —NH(CO)—$C_1$-$C_5$alkyl.

Further preferred styryl sulfide dyes correspond to formula

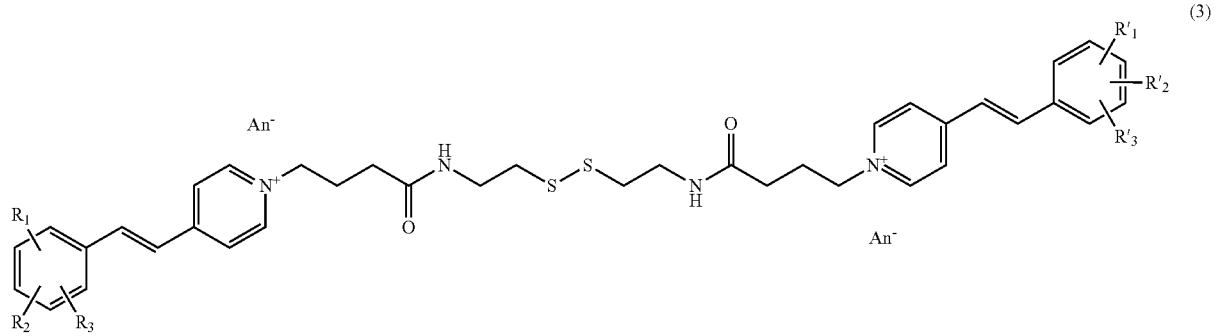

(3)

(4)
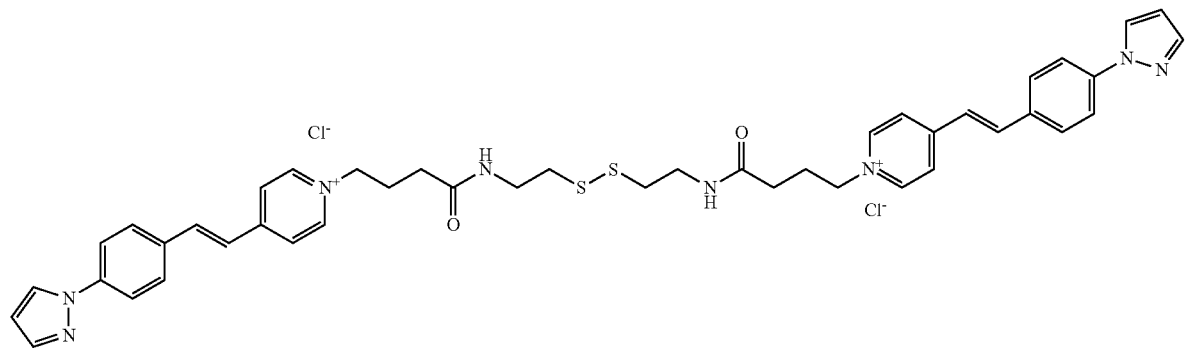
wherein
$R_1$, $R_2$, $R_3$, $R'_1$, $R'_2$ or $R'_3$ are defined as for formula (1).
The compounds of formula (1) may be present in its E/E-, E/Z- or Z/Z geometrical isomer forms.
Exemplary styryl sulfide dyes according to the present invention are listed in Table 1:
TABLE 1
Styryl sulfide dyes according to the present invention
| Comp | |
|---|---|
| (101) | |
| (102) | |
| (103) | |

TABLE 1-continued
Styryl sulfide dyes according to the present invention
Comp
(104)
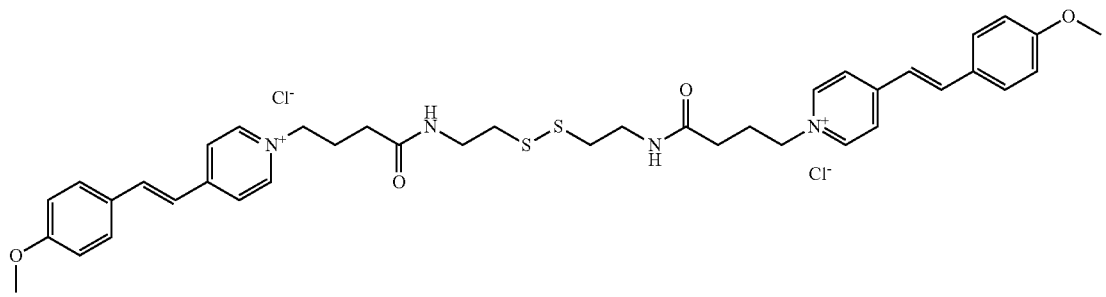 [SMILES: COc1ccc(/C=C/c2cc[n+](CCCC(=O)NCCSSCCNC(=O)CCC[n+]3ccc(/C=C/c4ccc(OC)cc4)cc3)cc2)cc1 ; [Cl-] ; [Cl-]]
(105)
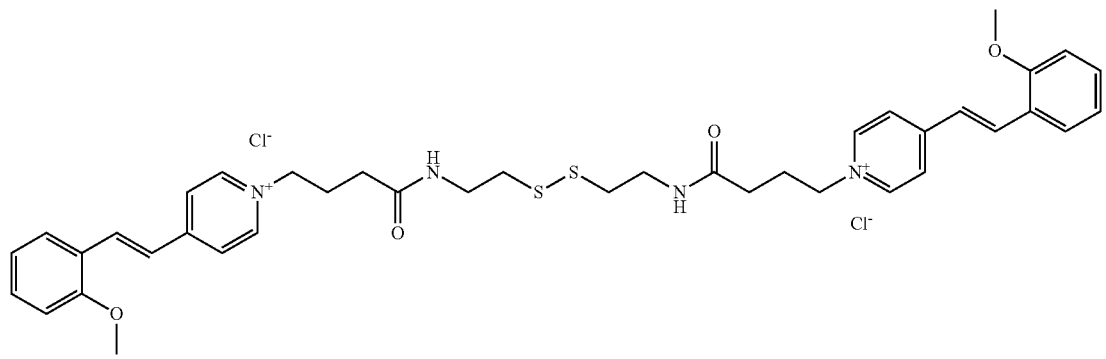 [SMILES: COc1ccccc1/C=C/c1cc[n+](CCCC(=O)NCCSSCCNC(=O)CCC[n+]2ccc(/C=C/c3ccccc3OC)cc2)cc1 ; [Cl-] ; [Cl-]]
(106)
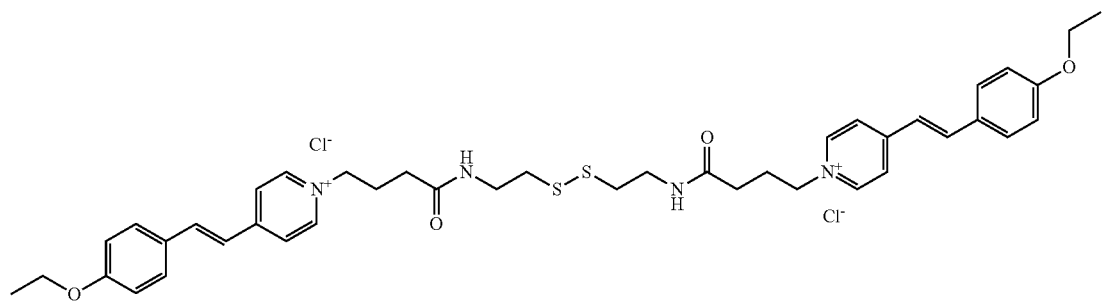 [SMILES: CCOc1ccc(/C=C/c2cc[n+](CCCC(=O)NCCSSCCNC(=O)CCC[n+]3ccc(/C=C/c4ccc(OCC)cc4)cc3)cc2)cc1 ; [Cl-] ; [Cl-]]
(107)
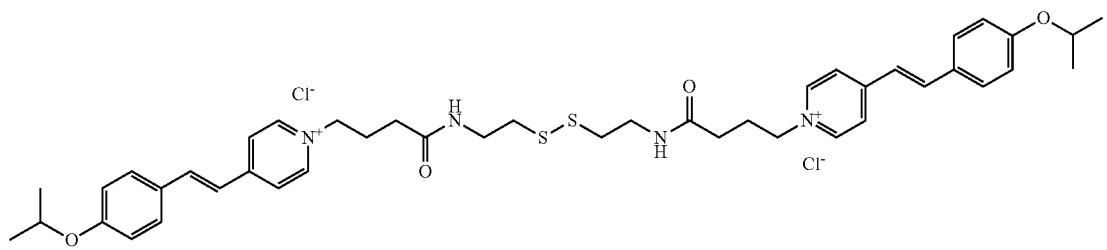 [SMILES: CC(C)Oc1ccc(/C=C/c2cc[n+](CCCC(=O)NCCSSCCNC(=O)CCC[n+]3ccc(/C=C/c4ccc(OC(C)C)cc4)cc3)cc2)cc1 ; [Cl-] ; [Cl-]]

TABLE 1-continued
Styryl sulfide dyes according to the present invention
Comp
(108)
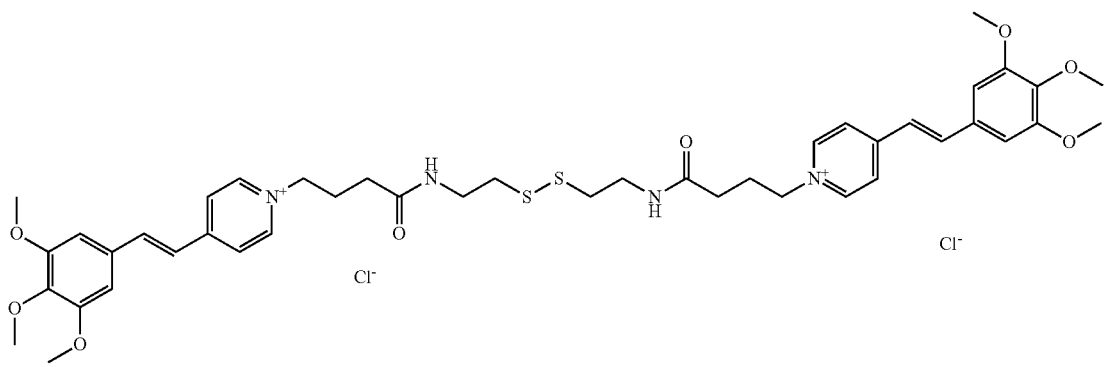 [SMILES: COc1cc(/C=C/c2cc[n+](CCCC(=O)NCCSSCCNC(=O)CCC[n+]3ccc(/C=C/c4cc(OC)c(OC)c(OC)c4)cc3)cc2)cc(OC)c1OC ; [Cl-] ; [Cl-]]
(109)
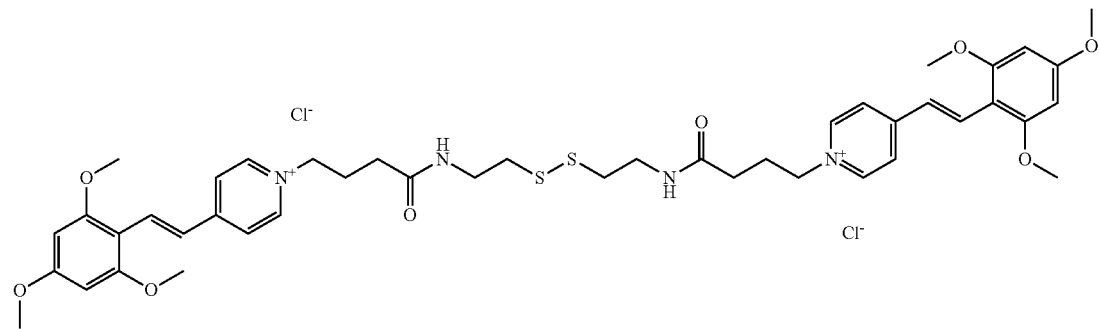 [SMILES: COc1cc(OC)c(/C=C/c2cc[n+](CCCC(=O)NCCSSCCNC(=O)CCC[n+]3ccc(/C=C/c4c(OC)cc(OC)cc4OC)cc3)cc2)c(OC)c1 ; [Cl-] ; [Cl-]]
(110)
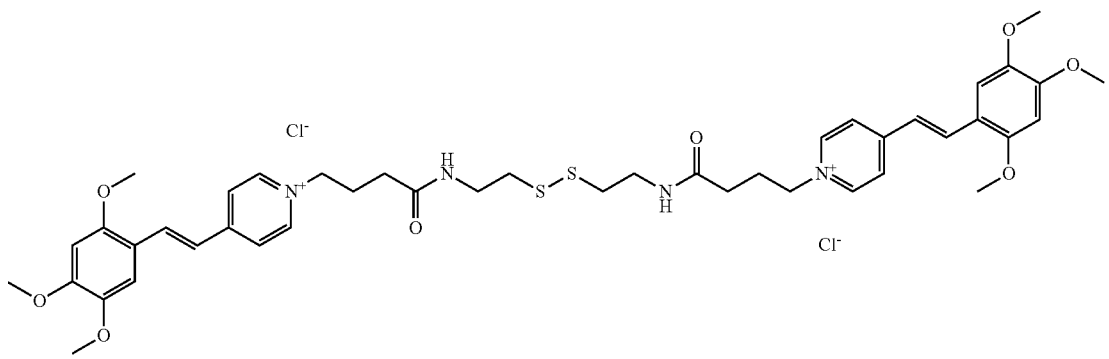
(111)
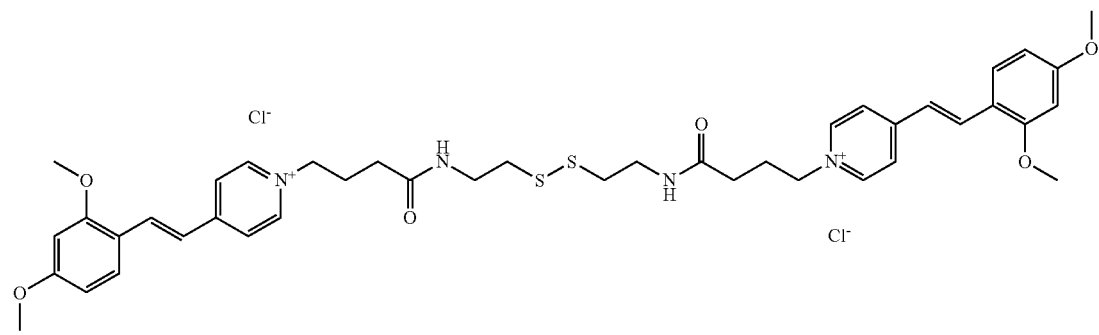 [SMILES: COc1ccc(/C=C/c2cc[n+](CCCC(=O)NCCSSCCNC(=O)CCC[n+]3ccc(/C=C/c4ccc(OC)cc4OC)cc3)cc2)c(OC)c1 ; [Cl-] ; [Cl-]]

TABLE 1-continued
Styryl sulfide dyes according to the present invention
Comp
(112)
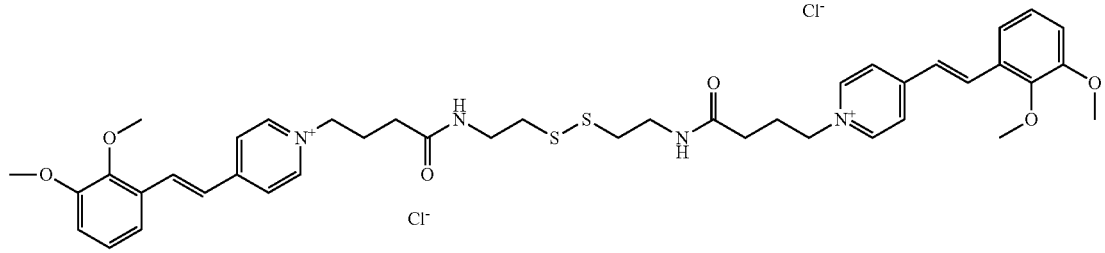
(113)
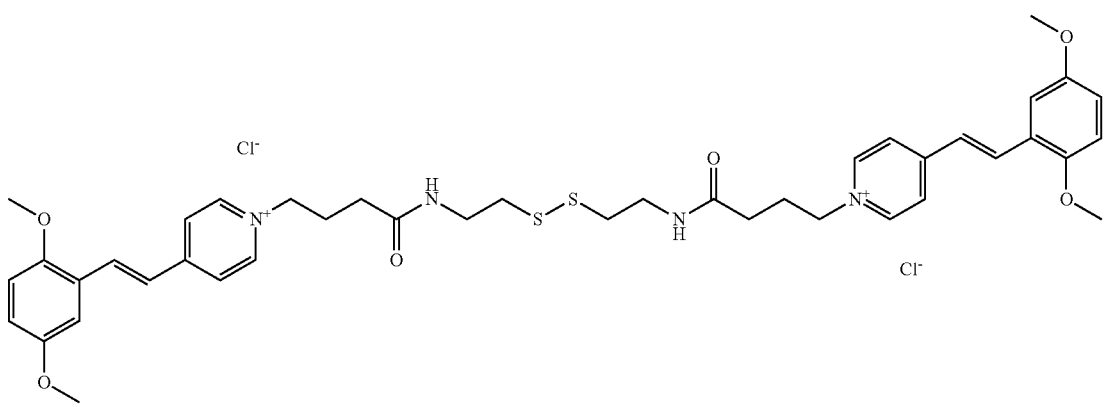 [SMILES: COc1ccc(OC)c(/C=C/c2cc[n+](CCCC(=O)NCCSSCCNC(=O)CCC[n+]3ccc(/C=C/c4cc(OC)ccc4OC)cc3)cc2)c1 ; [Cl-] ; [Cl-]]
(114)
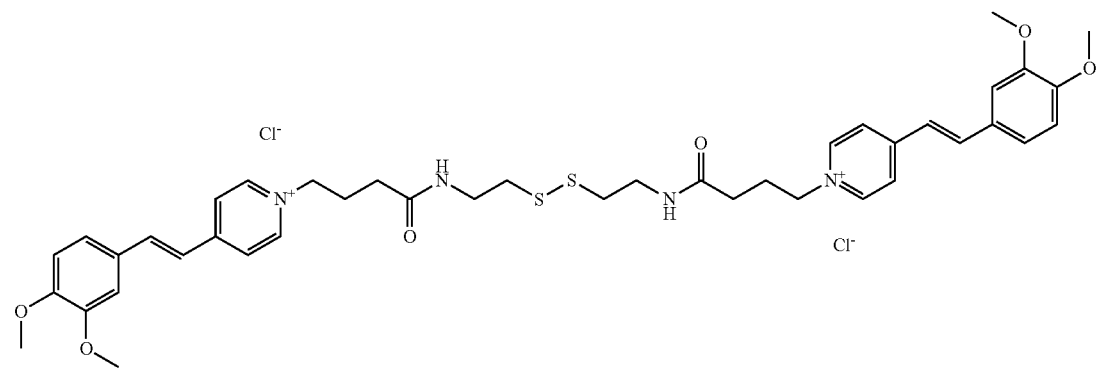 [SMILES: COc1ccc(/C=C/c2cc[n+](CCCC(=O)NCCSSCCNC(=O)CCC[n+]3ccc(/C=C/c4ccc(OC)c(OC)c4)cc3)cc2)cc1OC ; [Cl-] ; [Cl-]]
(115)
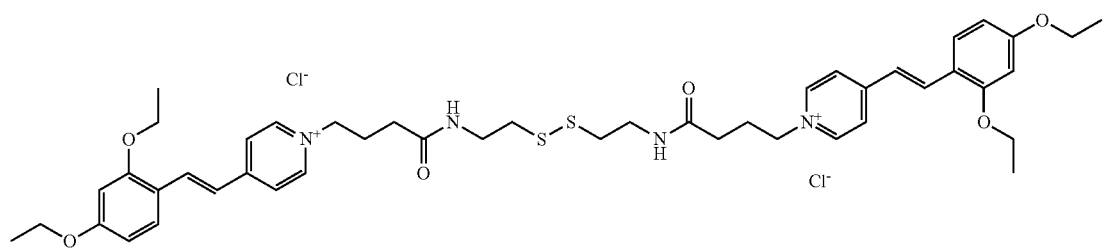 [SMILES: CCOc1ccc(/C=C/c2cc[n+](CCCC(=O)NCCSSCCNC(=O)CCC[n+]3ccc(/C=C/c4ccc(OCC)cc4OCC)cc3)cc2)c(OCC)c1 ; [Cl-] ; [Cl-]]

TABLE 1-continued

Styryl sulfide dyes according to the present invention

Comp (116)

(117)

(118)

(119)

TABLE 1-continued
Styryl sulfide dyes according to the present invention
Comp
(120)
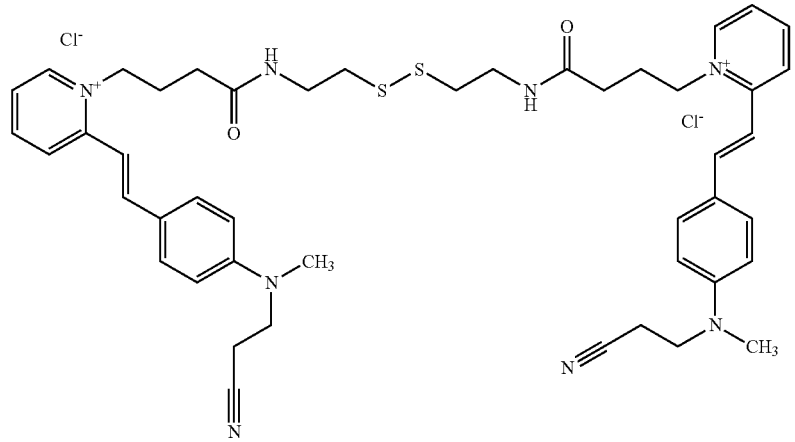 [SMILES: CN(CCC#N)c1ccc(/C=C/c2cccc[n+]2CCCC(=O)NCCSSCCNC(=O)CCC[n+]2ccccc2/C=C/c2ccc(N(C)CCC#N)cc2)cc1 ; [Cl-] ; [Cl-]]
(121)
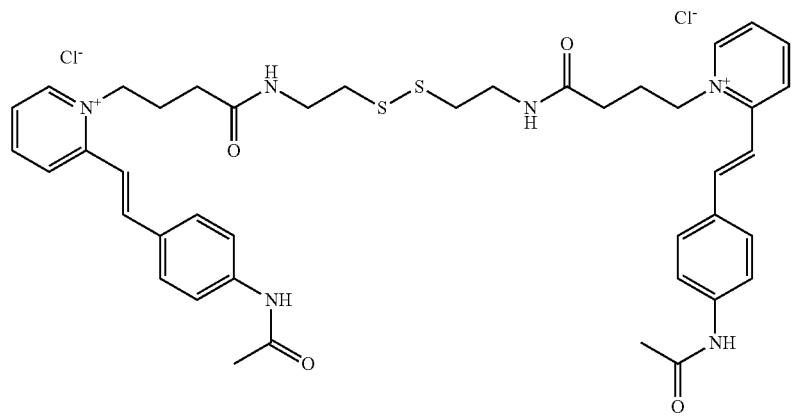 [SMILES: [Cl-] ; CC(=O)Nc1ccc(/C=C/c2cccc[n+]2CCCC(=O)NCCSSCCNC(=O)CCC[n+]2ccccc2/C=C/c2ccc(NC(C)=O)cc2)cc1 ; [Cl-]]
(122)
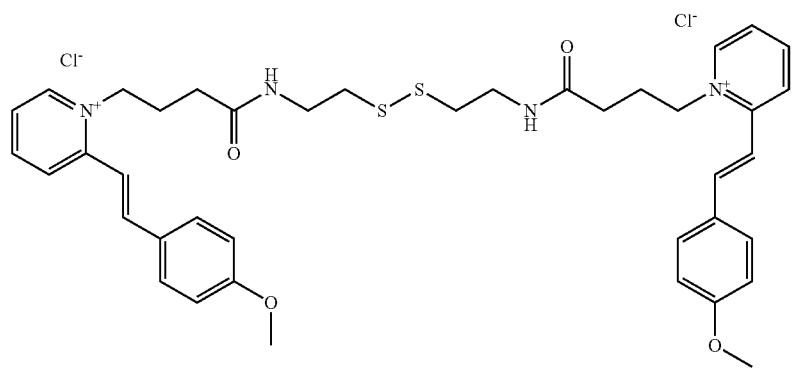 [SMILES: [Cl-] ; COc1ccc(/C=C/c2cccc[n+]2CCCC(=O)NCCSSCCNC(=O)CCC[n+]2ccccc2/C=C/c2ccc(OC)cc2)cc1 ; [Cl-]]
(123)
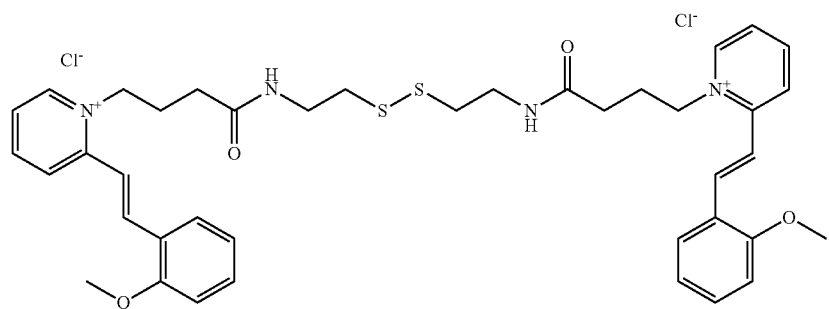 [SMILES: [Cl-] ; COc1ccccc1/C=C/c1cccc[n+]1CCCC(=O)NCCSSCCNC(=O)CCC[n+]1ccccc1/C=C/c1ccccc1OC ; [Cl-]]

TABLE 1-continued

Styryl sulfide dyes according to the present invention

Comp (124)

(125)

A further embodiment of the present invention relates to processes for the preparation of the dyes of formula (1).

The standard synthesis procedure of novel pyridinium styryl disulfide comprises of three synthetic steps. As disulfide starting material, cystamine or dithioethanol is used.

I: Synthesis Pathway Via Cystamine (Scheme 1)

Step 1 is the functionalization of the amino group of cystamine with an reactive aliphatic acid derivative to prepare the alkylation agent. An example for a reactive aliphatic acid derivative is chloro butyryl chloride. The condensation of cystamine and chlorobutyryl chloride to the halogenated intermediate I is performed under alkaline conditions according to literature procedures.

Step 2 is the alkylation of a reactive 2-picoline or 4-picoline with the alkylation agent prepared in step 1. Ethanol is used as a solvent and the reaction is done under reflux. A quaternized charged picoline derivative (intermediate II) is obtained.

Step 3 is a Knoevenagel condensation with a suitable substituted aromatic aldehyde. This reaction is performed in alcoholic solution in presence of a secondary amine. As solvent, ethanol or methanol is preferred, as secondary amine pyrrolidine is preferred.

All synthesis steps can be performed in high yield and the purification can be achieved by precipitation; no column chromatography is required.

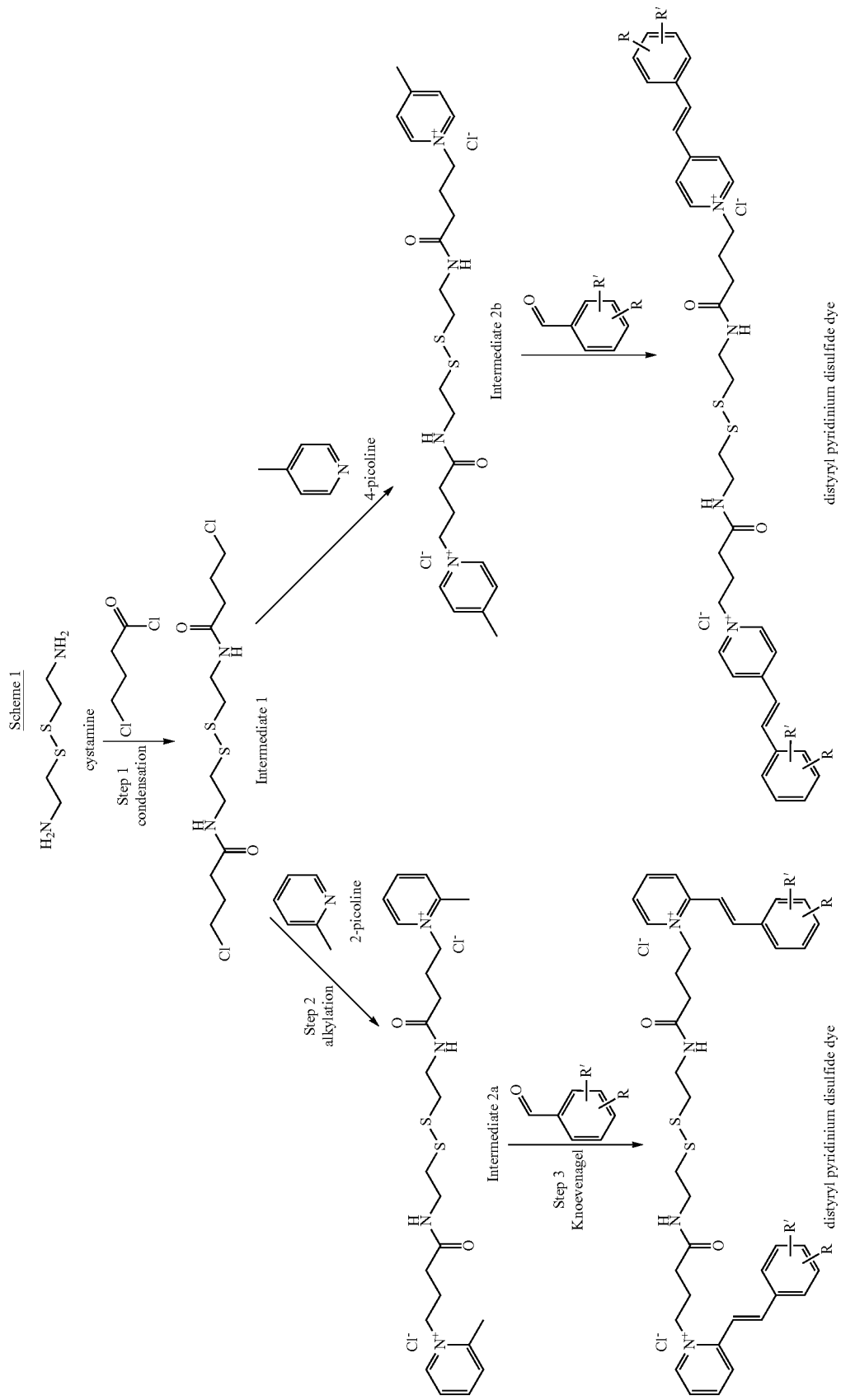

Similarly, those distyryl pyridinium disulfide dyes can be prepared from dithioethanol following very similar reaction pathway (Scheme 2). Dithioethanol can be transformed into the reactive bis-mesylate (Step 1). With that alkylation agent, picoline derivatives are reacted (Step 2). The corresponding charged intermediates are treated with a suitable modified benzaldehyde to obtain the distyryl pyridinium disulfide dyes The dyes of formula (1) according to the present invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing. The

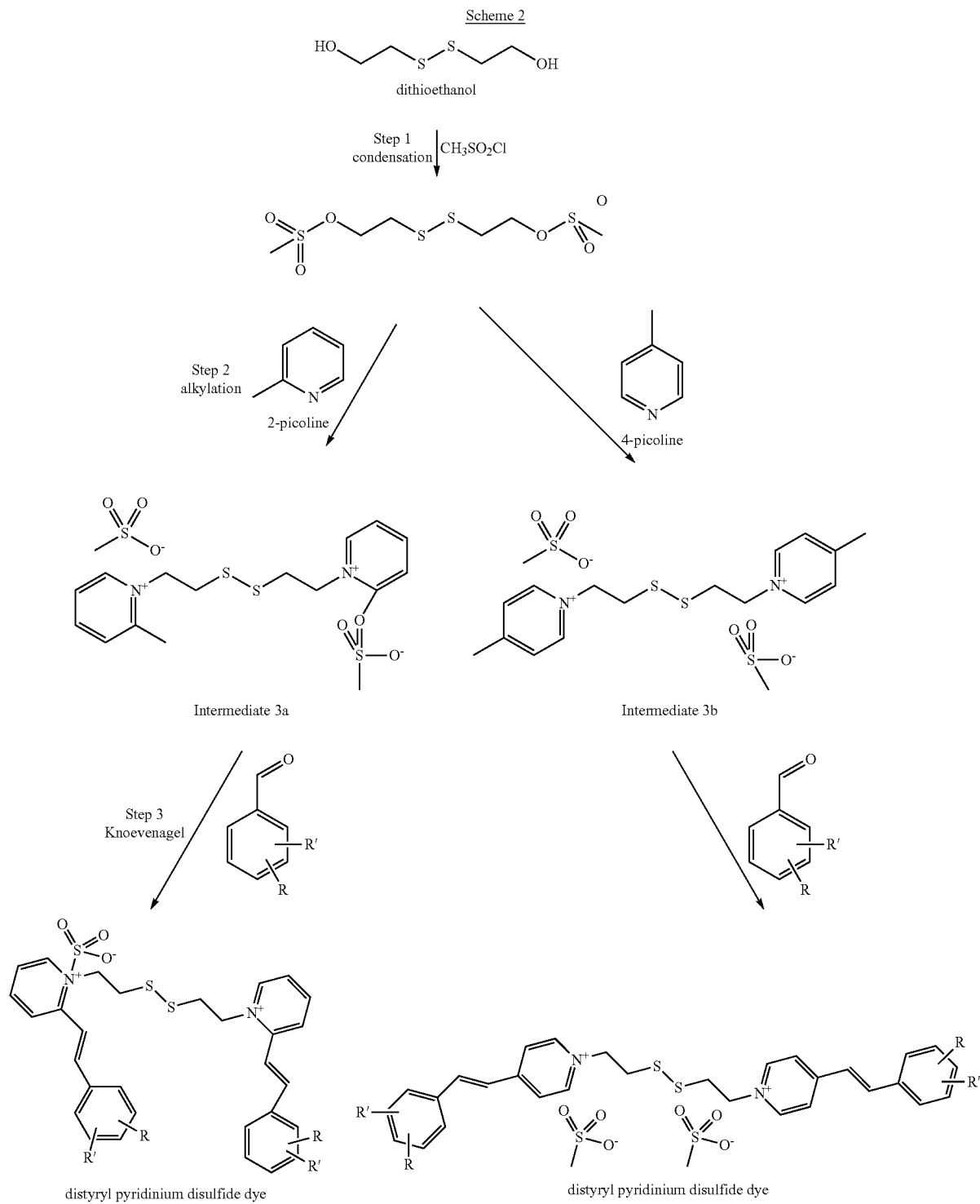

stability, in particular the storage stability of the dyes according to the invention are excellent.

Generally, hair dyeing agents on a synthetic base may be classified into three groups:
  temporary dyeing agents
  semipermanent dyeing agents, and
  permanent dyeing agents.

The multiplicity of shades of the dyes can be increased by combination with other dyes. Therefore the dyes of formula (1) of the present invention may be combined with dyes of the same or other classes of dyes, especially with direct dyes, oxidation dyes; dye precursor combinations of a coupler compound as well as a diazotized compound, or a capped diazotized compound and/or cationic reactive dyes.

Direct dyes are of natural origin or may be prepared synthetically. They are uncharged, cationic or anionic, such as acid dyes.

The dyes of formula (1) may be used in combination with at least one single direct dye different from the dyes of formula (1).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Guinan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie- und Handelsunternehmen für Arzneimittel, Reformwaren und Körperpflegemittel e.V., Mannheim.

More preferred direct dyes which are useful for the combination with at least one single dye of formula (1), especially for semi-permanent dyeing, are: 2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethylpicramic acid, 2,6-diamino-3-((pyridine-3yl)-azo)pyridine, 2-nitro-5-glyceryl-methylaniline, 3-methylamino-4-nitrophenoxyethanol, 4-amino-2-nitrodiphenyleneamine-2'-carboxilic acid, 6-nitro-1,2,3,4,-tetrahydroquinoxaline, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethyl-aminophenol, 4-amino-3-nitrophenol, 4-hydroxypropylamine-3-nitrophenol, hydroxyanthrylaminopropylmethyl morphlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, MC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, the dyes of formula (1) may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6 (compound of formula 106); or the cationic dye of formula (3) as described in EP-A-714,954, or with a yellow cationic dye of formula

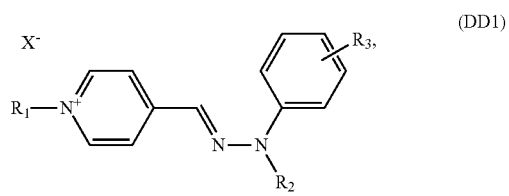

wherein
$R_1$ and $R_2$ are each independently of the other a $C_1$-$C_8$alkyl; or an unsubstituted or substituted benzyl;
$R_3$ is hydrogen; $C_1$-$C_8$alkyl; $C_1$-$C_8$alkoxy; cyanide; or halide; preferably hydrogen; and
$X^-$ is an anion; and preferably a compound of formula (DD1), wherein
$R_1$ is methyl; $R_2$ is benzyl; $R_3$ is hydrogen; and $X^-$ is an anion; or wherein
$R_1$ is benzyl; $R_2$ is benzyl; $R_3$ is hydrogen; and $X^-$ is an anion; or wherein
$R_1$ is benzyl; $R_2$ is methyl; $R_3$ is hydrogen; and $X^-$ is an anion.

Furthermore, cationic nitroaniline and anthraquinone dyes are useful for a combination with a dye of formula (1), for example the dyes as described in the following patent specifications: U.S. Pat. No. 5,298,029, especially in col 2, I. 33 to col 5, I. 38; U.S. Pat. No. 5,360,930, especially in col 2, I. 38 to col 5, I. 49; U.S. Pat. No. 5,169,403, especially in col 2, I. 30 to col 5, I. 38; U.S. Pat. No. 5,256,823, especially in col 4, I. 23 to col 5, I. 15; U.S. Pat. No. 5,135,543, especially in col 4, I. 24 to col 5. I. 16; EP-A-818 193, especially on p. 2, I. 40 to p. 3, I. 26; U.S. Pat. No. 5,486,629, especially in col 2, I. 34 to col 5, I. 29; and EP-A-758 547, especially on p. 7, I. 48 to p. 8, I. 19.

The dyes of formula (1) may also be combined with acid dyes, for example the dyes which are known from the international names (Color index), or trade names.

Preferred acid dyes which are useful for the combination with a dye of formula (1) are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof.

Hair dye compositions comprising an acid dye are known. They are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 253 and 254.

Hair dye compositions which comprise an acid dye have a pH of 2-6, preferably 2-5, more preferably 2.5-4.0.

The dyes of formula (1) according to the present invention may also readily be used in combination with acid dyes and/or adjuvants, for example acid dyes and an alkylene carbonate, as described in U.S. Pat. No. 6,248,314, especially in examples 1 and 2;

acid hair dye compositions comprising various kinds of organic solvents represented by benzyl alcohol as a penetrant solvent have good penetrability into hair, as described in Japanese Patent Application Laid-Open Nos. 210023/1986 and 101841/1995;

acid hair dye compositions with a water-soluble polymer or the like to prevent the drooping of the hair dye composition, as described for example in Japanese Patent Application Laid-Open Nos. 87450/1998, 255540/1997 and 245348/1996;

acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

The dyes of formula (1) may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the dyes of formula (1) may also be used in combination with oxidation dye systems.

Oxidation dyes, which, in the initial state, are not dyes but dye precursors are classified according to their chemical properties into developer and coupler compounds.

Suitable oxidation dyes are described for example in
DE 19 959 479, especially in col 2, I. 6 to col 3. I. 11;
"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes).

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraaminopyrimidine derivatives, or unsaturated aldehydes as described in DE 19 717 224, especially on p. 2, I. 50 to I. 66 and on p. 3 I. 8 to I. 12, or cationic developer compounds as described in WO 00/43367, especially on p., 2 I. 27 to p. 8. I. 24, in particular on p. 9, I. 22 to p. 11, I. 6.

Furthermore, developer compounds in their physiological compatible acid addition salt form, such as hydrochloride or sulfate can be used. Developer compounds, which have aromatic OH radicals are also suitable in their salt form together with a base, such as alkali metalphenolates.

Preferred developer compounds are disclosed in DE 19959479, p. 2, I. 8-29.

More preferred developer compounds are p-phenylendiamine, p-toluylendiamine, p-, m- o -aminophenol, N,N-bis-(2-hydroxyethyl)-p-phenylenediamine sulfate, 2-amino-4-hydroxyethylaminoanisole sulfate, hydroxyethyl-3,4-methylenedioxyaniline, 1-(2'-hydroxyethyl)-2,5-diaminobenzene, 2,6-dimethoxy-3,5-diamino-pyridine, hydroxypropyl-bis-(N -hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxy-ethyl)-1H-pyrazole, 4-amino-m-cresol, 6-amino-m-cresol, 5-amino-6-chloro-cresol, 2,4,5,6-tetraaminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p.1, I. 33 to p. 3, I. 11.

The dyes of formula (1) may also be used together with unsaturated aldehydes as disclosed in DE 19 717 224 (p. 2, I. 50 to 66 and on p. 3 I. 8 to I. 12) which may be used as direct dyes or, alternatively together with oxidation dye precursors.

Further preferred for a combination with a dye of formula (1) are the following oxidation dye precursors:

the developer/-coupler combination 2,4,5,6-tetraaminopyrimidine and 2-methylresorcine for assessing of red shades;

p-toluenediamine and 4-amino-2-hydroxytoluene for assessing of blue-violet shades;

p-toluenediamine and 2-amino-4-hydroxyethylaminoanisole for assessing of blue shades;

p-toluenediamine and 2,4-diamino-phenoxyethynol for assessing of blue shades;

methyl-4-aminophenol and 4-amino-2-hydroxytleoluene for assessing of orange shades;

p-toluenediamine and resorcine for assessing of brown-green shades;

p-toluenediamine and 1-naphthol for assessing of blue-violet shades, or p-toluenediamine and 2-methylresorcine for assessing of brown-gold shades.

Furthermore, autooxidizable compounds may be used in combination with the dyes of formula (1).

Autooxidizable compounds are aromatic compounds with more than two substituents in the aromatic ring, which have a very low redox potential and will therefore be oxidized when exposed to the air. The dyeings obtained with these compounds are very stable and resistant to shampoo.

Autooxidizable compounds are for example benzene, indole, or indoline, especially 5,6-dihydroxyindol or 5,6-dihydroxyindoline derivatives as described in WO 99/20234, especially on p. 26, I. 10 to p. 28, I. 15, or in WO 00/28957 on p. 2, third paragraph.

Preferred autooxidizable benzene derivatives are 1,2,4-trihydroxybenzene, 1-methyl-2,4,5-trihydroxybenzene, 2,4-diamnio-6-methylphenol, 2-amino-4-methylaminophenol, 2,5-diamino-4-methyl-phenol, 2,6-diamino-4-diethylaminophenol, 2,6-diamino-1,4-dihydroxy-benzene, and the salts of these compounds, which are accessible with acid.

Preferred autooxidizable indole derivatives are 5,6-dihydroxyindol, 2-methyl-5,6-dihydroxy-indol, 3-methyl-5,6-dihydroxyindole, 1-methyl-5,6-dihydroxyindol, 2,3-dimethyl-5,6-dihydroxy-indol, 5-methoxy-6-dihydroxyindol, 5-acetoxy-6-hydroxyindol, 5,6-diacetoxyindol, acid of 5,6-dihydroxyindol-2-carbonacid, and the salts of these compounds, which are accessible with acid.

The dyes of formula (1) may also be used in combination with naturally occurring dyes, such as henna red, henna neutral, henna black, camomile blossom, sandalwood, black tea, Rhamnus frangula bark, sage, campeche wood, madder root, catechu, sedre and alkanet root. Such dyeings are described, for example, in EP-A-404 868, especially on p. 3, I. 55 to p. 4, I. 9.

Furthermore, the dyes of formula (1) may also be used in combination with capped diazotized compounds.

Suitable diazotized compounds are for example the compounds of formulae (1)-(4) in WO 2004/019897 (bridging gages 1 and 2) and the corresponding watersoluble coupling components (I)-(IV) as disclosed in the same reference.

Further preferred dyes or dye combinations which are useful for the combination with a dye of formula (1) according to the present invention are described in (DC-01): WO 95/01772, wherein mixtures of at least two cationic dyes are disclosed, especially p. 2, I. 7 to p. 4, I. 1, preferably p. 4, I. 35 to p. 8, I. 21; formulations p. 11, last §—p. 28, I. 19;

(DC-02): U.S. Pat. No. 6,843,256, wherein cationic dyes are disclosed, especially the compounds of formulae (1), (2), (3) and (4) (col. 1, I. 27-col. 3, I. 20, and preferably the compounds as prepared in the examples 1 to 4 (col. 10, I.42 to col. 13, I. 37; formulations col. 13, I. 38 to col. 15, I. 8;

(DC-03): EP 970 685, wherein direct dyes are described, especially p. 2, I. 44 to p. 9, I. 56 and preferably p. 9, I. 58 to p. 48, I. 12; processes for dyeing of keratin-containing fibers especially p. 50, I. 15 to 43; formulations p. 50, I. 46 to p. 51, I. 40;

(DC-04): DE-A-19 713 698, wherein direct dyes are described, especially p. 2, I. 61 to p. 3, I. 43; formulations p. 5, I. 26 to 60;

(DC-05): U.S. Pat. No. 6,368,360, wherein directd dyes (col. 4, I. 1 to col. 6, I. 31) and oxidizing agents (col. 6, I. 37 -39) are disclosed; formulations col. 7, I. 47 to col. 9, I. 4;

(DG-06): EP 1 166 752, wherein cationic dyes (p. 3, I. 22-p. 4, I. 15) and anionic UV-absorbers (p. 4, I. 27-30) are disclosed; formulations p. 7, I. 50-p. 9, I. 56;

(DC-07): EP 998,908, wherein oxidation dyeings comprising a cationic direct dye and pyrazolo-[1,5-a]-pyrimidines (p. 2, I. 48-p. 4, I. 1) are disclosed; dyeing formulations p. 47, I. 25 to p. 50, I. 29;

(DC-08): FR-2788432, wherein combinations of cationic dyes with Arianors are disclosed, especially p. 53, I. 1 to p. 63, I. 23, more especially p. 51 to 52, most especially Basic) Brown 17, Basic brown 16, Basic Red 76 and Basic Red 118, and/or at least one Basic Yellow 57, and/or at least one Basic Blue 99; or combinations of arianors and/or oxidative dyes, especially p. 2, I. 16 to p. 3, I. 16; dyeing formulations on p. 53, I. 1 to p. 63, I. 23;

(DC-09): DE-A-19 713 698, wherein the combinations of direct dyes and permanent-wave fixing comprising an oxidation agent, an oxidation dye and a direct dye are disclosed; especially p. 4, I. 65 to p. 5, I. 59;

(DC-10): EP 850 638, wherein developer compounds and oxidizing agents are disclosed; especially p. 2, I. 27 to p. 7, I. 46 and preferably p. 7, I. 20 to p. 9, I. 26; dyeing formulations p. 2, I. 3-12 and I. 30 to p. 14, and p. 28, I. 35-p. 30, I. 20; preferably p. 30. I. 25-p. 32, I. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, I. 40-col. 7, I. 14), optionally dispersed in an organic pulverulent excipient and/or a mineral pulverulent excipient, and a composition (C) containing one or more oxidizing agents are disclosed; formulations col. 8, I. 60-col. 9, I. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, I. 17-col. 13, I. 65; dyeing formulations in col. 2, I. 16 to col. 25, I. 55, a multi-compartment dyeing device is described in col. 26, I. 13-24;

(DC-13): WO 99/20235, wherein compositions of at least one cationic dye and at least one nitrated benzene dye with cationic direct dyes and nitro benzene direct dyes are described; on p. 2, I. 1 to p. 7, I. 9, and p. 39, I. 1 to p. 40 I. 11, preferably p. 8, I. 12 to p. 25 I. 6, p. 26, I. 7 to p. 30, I. 15; p. 1, I. 25 to p. 8, I. 5, p. 30, I. 17 to p. 34 I. 25, p. 8, I. 12 to p. 25 I. 6, p. 35, I. 21 to 27, especially on p. 36, I. 1 to p. 37;

(DC-14): WO 99/20234, wherein compositions comprising at least one direct cationic dye and at least one autooxidisable dye, especially benzene, indol and indoline derivatives are described, preferably direct dyes on p. 2. I. 19 to p. 26. I. 4, and autooxidizable dyes as disclosed especially on p. 26, I. 10 to p. 28, I. 15; dyeing formulations especially on p. 34, I. 5 to p. 35, Ii 18;

DC-15): EP 850 636, wherein oxidation dyeing compositions comprising at least one direct dye and at least one meta-aminophenol derivative as coupler component and at least one developer compound and an oxidizing agent are disclosed, especially p. 5, I. 41 to p. 7, I. 52, dyeing formulations p. 19, I. 50-p. 22. I. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, I. 50 to p. 8, I. 44 are disclosed; dyeing formulations p. 21, I. 30-p. 22, I. 57;

(DC-17): WO 99/48856, wherein oxidation dyeing compositions comprising cationic couplers are disclosed, especially p. 9, I. 16-p. 13, I. 8, and p. 11, I. 20-p. 12, I. 13; dyeing formulations p. 36, I. 7-p. 39, I. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptids, aromatic hydroxy compounds, and/or at least one CH-active compound are disclosed p. 3, I. 42-p. 5 I. 25; dyeing formulations p. 8, I. 25-p. 9, I. 61.

In the dye combinations disclosed in the references (DC-01-DC-18) above, the dyes of formula (1) according to the present invention may be added to the dye combinations or dyeing formulations or may be replaced with at least one dye of formula (1).

Hair dyeing formulations comprise at least
(a) 0.001 to 5, preferably 0.005 to 4, more particularly 0.2 to 3% b.w. of at least one dye of formula (1);
(b) 1 to 40, preferably 5 to 30% b.w. of a solvent; and
(c) 0.01 to 20% b.w. of an adjuvant.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, a gel, or an emulsion.

Customary the dyeing compositions are applied to the keratin-containing fiber in an amount of 50 to 100 g.

The dyeing compositions of the present invention are applied on the hair in a temperature range of 25 to 200, preferably 18 to 80, and most preferably from 20 to 40° C.

Preferred forms of formulations are ready-to-use compositions or multi-compartment dyeing devices or 'kits' or any of the multi-compartment packaging systems with compartments as described for example in U.S. Pat. No. 6,190,421, col 2, I. 16 to 31.

One preferred method of applying formulations comprising the dyes of formula (1) on the keratin-containing fiber, preferably the hair is by using a multi-compartment dyeing device or "kit" or any other multi-compartment packaging system, as described for example in WO 97/20545 on p. 4, I. 19 to I. 27.

The first compartment contains for example at least one dye of formula (1) and optionally further direct dyes and a basifying agent, and in the second compartment an oxidizing agent; or in the first compartment at least one dye of formula (1) and optionally further direct dyes, in the second compartment a basifying agent and in the third compartment an oxidizing agent.

The pH value of the ready-to-use dyeing compositions is usually from 2 to 11, preferably from 5 to 10.

Preferably the dyeing compositions, which are not stable to reduction, are prepared with oxidizing agent free compositions just before the dyeing process.

Suitable formulations of dyes are those, wherein the dyes of formula (1) are in powder form, Powder formulations are preferably used if stability and/or solubility problems as for example described in DE 197 13098, p. 2, I. 26 to 54 and p. 3. I. 51 to p. 4, I. 25, and p. 4, I. 41 to p. 5 I. 59, occur.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions are also excellently suitable for the dyeing method described in DE-A-3 829 870 using a dyeing comb or a dyeing brush.

The constituents of the aqueous carrier are present in the dyeing compositions in customary amounts, for example emulsifiers may be present in the dyeing compositions in concentrations from 0.5 to 30% b.w. and thickeners in concentrations from 0.1 to 25% b.w. of the total dyeing composition.

Further carriers for dying compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

A shampoo has, for example, the following composition:
0.01 to 5 % b.w. of the dye of formula (1);
8% b.w of disodium PEG-5 lauryl citrate Sulfosuccinate, Sodium Laureth Sulfate;
20% b.w. of sodium cocoamphoacetate;
0.5% b.w. of methoxy PEG/PPG-7/3 aminopropyl dimethicone;
0.3% b.w. of hydroxypropyl guar hydroxypropytrimonium chloride;
2.5% b.w. of PEG-200 hydrogenated glyceryl palmate; PEG-7 glyceryl cocoate;
0.5% b.w. of PEG-150 distearate;
2.2.% b.w of citric acid;
perfume, preservatives; and
water ad 100 %.

The dyes of formula (1) may be stored in a liquid to paste-like preparation (aqueous or non-aqueous) or in the form of a dry powder.

When the dyes and adjuvants are stored together in a liquid preparation, the preparation should be substantially anhydrous in order to reduce reaction of the compounds.

The dyeing compositions may comprise any active ingredients, additives or adjuvants known for such preparations, like surfactants, solvents, bases, acids, perfumes, polymeric adjuvants, thickeners and light stabilizers.

The following adjuvants are preferably used in the hair dyeing compositions of the present invention:
non-ionic polymers, for example vinylpyrrolidone/vinyl acrylate copolymers, polyvinylpyrrolidone and vinylpyrrolidone/vinyl acetate copolymers and polysiloxanes;
cationic polymers, such as quaternised cellulose ethers, polysiloxanes having quaternary groups, dimethyldiallylammonium chloride polymers, copolymers of dimethyldiallyl-ammonium chloride and acrylic acid, as available commercially under the name Merquat® 280 and the use thereof in hair dyeing as described, for example, in DE-A-4 421 031, especially p. 2, I. 20 to 49, or EP-A-953 334;
acrylamide/dimethyldiallylammonium chloride copolymers, diethyl-sulfate-quaternised dimethylaminoethyl methacrylate/vinylpyrrolidone copolymers, vinylpyrrolidone/-imidazolinium methochloride copolymers;
quaternised polyvinyl alcohol:
zwitterionic and amphoteric polymers, such as acrylamido-propyltrimethylammonium chloride/acrylate copolymers and octylacrylamide/methyl methacrylate/tert-butylaminoethyl methacrylate/2-hydroxypropyl methacrylate copolymers;
anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers;

thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol;

structuring agents, such as glucose and maleic acid;

hair-conditioning compounds, such as phospholipids, for example soya lecithin, egg lecithin, cephalins, silicone oils, and conditioning compounds, such as those described in DE-A-19 729 080, especially p. 2, I. 20 to 49, EP-A-834 303, especially p. 2, I. 18-p. 3, I. 2, or EP-A-312 343, especially p. 2, I. 59-p. 3, I. 11;

protein hydrolysates, especially elastin, collagen, keratin, milk protein, soya protein and wheat protein hydrolysates, condensation products thereof with fatty acids and also quaternised protein hydrolysates;

perfume oils, dimethyl isosorbitol and cyclodextrins, solubilizers, such as ethanol, isopropanol, ethylene glycol, propylene glycol, glycerol and diethylene glycol, anti-dandruff active ingredients, such as piroctones, olamines and zinc Omadine, substances for adjusting the pH value;

panthenol, pantothenic acid, allantoin, pyrrolidonecarboxylic acids and salts thereof, plant extracts and vitamins;

cholesterol;

light stabilizers and UV absorbers as listed in Table below:

TABLE 2

UV absorbers which may be used in the dyeing compositions of the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxy cinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |
| 18 | Benzoic acid, 4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy]-phenyl}-6-(4-methoxyphenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexyl ester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-a-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 37 | 2-Hydroxy-4-methoxy benzophenone-5-sulfonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |

TABLE 2-continued

UV absorbers which may be used in the dyeing compositions of the present invention

| No. | Chemical Name | CAS No. |
|---|---|---|
| 42 | 3,3'-(1,4-phenylenedimethylene)bis[7,7-dimethyl-2-oxo-bicyclo[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]-propyl]N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |
| 48 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |

Furthermore, the following combinations may be used in the dyeing compositions:

cationic benzotriazole UV absorbers as for example described in WO 01/36396 especially on p. 1, I. 20 to p. 2, I. 24, and preferred on p. 3 to 5, and on p. 26 to 37;

cationic benzotriazole UV in combination with antioxidants as described in WO 01/36396, especially on p. 11, I. 14 to p. 18;

UV absorbers in combination with antioxidants as described in U.S. Pat. No. 5,922,310, especially in col 2, I. 1 to 3;

UV absorbers in combination with antioxidants as described in U.S. Pat. No. 4,786,493, especially in col 1, 42 to col 2, I. 7, and preferred in col 3, 43 to col 5, I. 20;

combination of UV absorbers as described in U.S. Pat. No. 5,830,441, especially in col 4, I. 53 to 56;

combination of UV absorbers as described in WO 01/36396, especially on p. 11, I. 9 to 13; or triazine derivatives as described in WO 98/22447, especially on p. 1, I. 23 to p. 2, I. 4, and preferred on p. 2, I. 11 to p. 3, I. 15 and most preferred on p. 6 to 7, and 12 to 16. Suitable cosmetic preparations may usually contain from 0.05 to 40% b.w., preferably from 0.1 to 20% b.w., based on the total weight of the composition, of one or more UV absorbers;

consistency regulators, such as sugar esters, polyol esters or polyol alkyl ethers;

fats and waxes, such as spermaceti, beeswax, montan wax, paraffins, fatty alcohols and fatty acid esters;

fatty alkanolamides;

polyethylene glycols and polypropylene glycols having a molecular weight of from 150 to 50 000, for example such as those described in EP-A-801 942, especially p. 3, I. 44 to 55, complexing agents, such as EDTA, NTA and phosphonic acids, swelling and penetration substances, such as polyols and polyol ethers, as listed extensively, for example, in EP-A-962 219, especially p. 27, I. 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole;

opacifiers, such as latex;

pearlising agents, such as ethylene glycol mono- and di-stearate;

propellants, such as propane-butane mixtures, $N_2O$, dimethyl ether, $CO_2$ and air;

antioxidants; preferably the phenolic antioxidants and hindered nitroxyl compounds disclosed in ip.com (IP-COM #000033153D);

sugar-containing polymers, as described in EP-A-970 687;

quaternary ammonium salts, as described in WO 00/10517;

Bacteria inhibiting agents, like preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% b.w., based on the solids content of the preparations;

The dyeing compositions generally comprise at least one surfactant. Suitable surfactants are zwitterionic or ampholytic, or more preferably anionic, non-ionic and/or cationic surfactants.

Suitable anionic surfactants in the dyeing compositions include all anionic surface-active substances that are suitable for use on the human body. Such substances are characterized by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanol ammonium salts having 2 or 3 carbon atoms in the alkanol group:

linear fatty acids having 10 to 22 carbon atoms (soaps),
ether carboxylic acids of formula R—O—($CH_2$—$CH_2$—O)$_x$—$CH_2$—COOH, in which R is a linear alkyl group having 10 to 22 carbon atoms and $n=0$ or from 1 to 16,
acyl sarcosides having 10 to 18 carbon atoms in the acyl group,
acyl taurides having 10 to 18 carbon atoms in the acyl group,
acyl isothionates having 10 to 18 carbon atoms in the acyl group,
sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups,
linear alkane sulfonates having 12 to 18 carbon atoms,
linear α-olefin sulfonates having 12 to 18 carbon atoms,
α-sulfo fatty acid methyl esters of fatty acids having 12 to 18 carbon atoms,
alkyl sulfates and alkyl polyglycol ether sulfates of formula R'—O($CH_2$—$CH_2$—O)$_x$—$SO_3$H, in which R' is a preferably linear alkyl group having 10 to 18 carbon atoms and x'=0 or from 1 to 12,
mixtures of surface-active hydroxysulfonates according to DE-A-3 725 030;
sulfated hydroxyalkylpolyethylene and/or hydroxyalkylenepropylene glycol ethers according to DE-A-3 723 354, especially p. 4, I. 42 to 62,
sulfonates of unsaturated fatty acids having 12 to 24 carbon atoms and 1 to 6 double bonds according to DE-A-3 926 344, especially p. 2, I. 36 to 54,
esters of tartaric acid and citric acid with alcohols which are addition products of approximately from 2 to 15 molecules of ethylene oxide and/or propylene oxide with fatty alcohols having from 8 to 22 carbon atoms, or
anionic surfactants, as described in WO 00/10518, especially p. 45, I. 11 to p. 48, I. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$carboxylic acids, such as oleic acid, stearic acid, isostearic acid and palmitic acid.

Surface-active compounds that carry at least one quaternary ammonium group and at least one —COO$^-$ or —$SO_3^-$ group in the molecule are terminated zwitterionic surfactants. Preference is given the so-called betaines, such as the N-alkylN,N-dimethylammonium glycinates, for example cocoalkyldimethylammonium glycinate. N-acylaminopropyl-N,N-dimethylammonium glycinates, for example cocoacylaminopropyldimethylammonium glycinate, and 2-alkyl-3-carboxymethyl-3-hydroxyethylimidazoline having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —$SO_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, I. 11 to p. 50, I. 12. Non-ionic surfactants contain as hydrophilic group, for example, a polyol group, a polyalkylene glycol ether group or a combination of polyol and polyglycol ether groups. Such compounds are, for example:

addition products of 2 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group,
$C_{12}$-$C_{22}$ fatty acid mono- and di-esters of addition products of 1 to 30 mol of ethylene oxide with glycerol.
$C_8$-$C_{22}$alkyl-mono- and -oligo-glycosides and ethoxylated analogues thereof,
addition products of 5 to 60 mol of ethylene oxide with castor oil and hydrogenated castor oil,
addition products of ethylene oxide with sorbitan fatty acid esters,
addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethy-lammonium chloride, lauryldimethylammonium chloride, lautyldimethylbenzylammonium chloride and tricetyl-methylammonium chloride. Further cationic surfactants that can be used are quaternised protein hydrolysates.

Also suitable are cationic silicone oils, such as, for example, the commercially available products Q2-7224 (manufacturer: Dow Corning; a stabilized trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, I. 9 to p. 55, I. 2.

Alkylamidoamines, especially fatty acid amidoamines, such as the stearylamidopropyl-dimethylamine obtainable under the name Tego Amid® 18 are also preferred as surfactants in the present dyeing compositions. They are distinguished not only by a good conditioning action but also especially by their good biodegradability.

Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquat®100, according to CTFA nomenclature a "lauryl methyl gluceth-10 hydroxypropyl diammonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The keratin-containing fibers are preferably treated with styryl sulfide dyes of formula (1) in the presence of a reducing agent.

Preferred reduction agents are for example thioglycolic acid or salts therof, gycerine mono-thioglycolate, cysteine, homocysteine, 2-mercaptopropionic acid, 2-mercaptoethylamine, thioiactic acid and the salts thereof, thioglycerine, sodium sulfite, dithionithe, ammonium sulfite, sodium bisulfite, sodium metabisulfite, hydrochinon or phosphites.

Preferred methods are:
a. treating the keratin-containing fibers with a compound of formula (1),
b. wearing the colored hair for the desired period of time,
c. removing the color applied in step a. from hair by contacting the hair with an aqueous based color removal composition containing a reduction agent capable of disrupting the —S—S-bonds between the dye molecule and the hair fiber surface to cause the dye molecule to become disassociated from the hair fiber.

Further preferred methods are treating the hair with
a. a reduction agent, and
b. at least one single styryl sulfide dye of formula (1) as defined above, and optionally
c. with an oxidizing agent.

The sequence of the reaction steps is generally not important, the reduction agent can be applied first or in a final step.

Preferred is a process, which comprises treating the hair
a$_1$) with at least one single dye of formula (1), and
b$_1$) then with a reduction agent; or
a process, which comprises treating the hair
a$_2$) with a reduction agent and
b$_2$) then with at least one single sulfide dye of formula (1) as defined above.

Preferred is further a process, which comprises treating the hair
a) with a reduction agent,
b) then with at least one dye of formula (1), and
c) then with an oxidizing agent.

A further process comprises contacting hair
a) with at least one single dye of formula (1),
b) then with a reduction agent, and
c) then with an oxidizing agent.

Usually, the oxidizing agent is applied together with an acid or a base.

The acid is for example citric acid, phosphoric acid or tartrate acid.

The base is for example sodium hydroxide, ammonia or monoethanolamine.

The dyes of formula (1) are suitable for all-over dyeing of the hair, that is to say when dyeing the hair on a first occasion, and also for re-dyeing subsequently, or dyeing of locks or parts of the hair.

The dyes of formula (1) are applied on the hair for example by massage with the hand, a comb, a brush, or a bottle, or a bottle, which is combined with a comb or a nozzle.

In the processes for dyeing, whether or not dyeing is to be carried out in the presence of a further dye will depend upon the color shade to be obtained.

Further preferred is a process for dyeing keratin-containing fibers which comprises treating the keratin-containing fiber with at least one dye of formula (1), a base and an oxidizing agent.

The oxidation dyeing process usually involves lightening, that is to say that it involves applying to the keratin-containing fibers, at basic pH, a mixture of bases and aqueous hydrogen peroxide solution, leaving the applied mixture to stand on the hair and then rinsing the hair. It allows, particularly in the case of hair dyeing, the melanin to be lightened and the hair to be dyed.

Lightening the melanin has the advantageous effect of creating a unified dyeing in the case of grey hair, and, in the case of naturally pigmented hair, of bringing out the color, that is to say of making it more visible.

In general, the oxidizing agent containing composition is left on the fiber for 0 to 15 minutes, in particular for 0 to 5 minutes at 15 to 45° C., usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are
oxidizing agents to achieve lightened coloration, as described in WO 97/20545, especially p. 9, I. 5 to 9,
oxidizing agents in the form of permanent-wave fixing solution, as described in DE-A-19 713 698 , especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

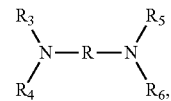

wherein

R is a propylene residue, which may be substituted with OH or $C_1$-$C_4$alkyl, $R_3$, $R_4$, $R_5$ and $R_6$ are independently or dependently from each other hydrogen, $C_1$-$C_4$alkyl or hydroxy-($C_1$-$C_4$) alkyl.

The pH-value of the oxidizing agent containing composition is usually about 2 to 7, and in particular about 2 to 5.

One preferred method of applying formulations comprising the dyes of formula (1) on the keratin-containing fiber, preferably the hair is by using a multi-compartment dyeing device or "kit" or any other multi-compartment packaging system, as described for example in WO 97/20545 on p. 4, I. 19 to I. 27.

The first compartment contains for example at least one dye of formula (1) and optionally further direct dyes and a basifying agent, and in the second compartment an oxidizing agent; or in the first compartment at least one dye of formula (1) and optionally further direct dyes, in the second compartment a basifying agent and in the third compartment an oxidizing agent.

Generally the hair is rinsed after treatment with the dyeing solution and/or permanent-wave solution.

A further preferred method of dyeing hair with oxidative dyes comprises a. mixing at least one dye of formula (1) and optionally at least one coupler compound and at least one developer compound, and an oxidizing agent, which optionally contains at least one further dye, and
b. contacting the keratin-containing fibers with the mixture as prepared in step a.

The pH-value of the oxidizing agent free composition is usually from 3 to 11, and in particular from 5 to 10, and most particular about 9 to 10.

Preferably, a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler, especially selected from meta-phenylenediamines and the acid-addition salts thereof, and at least one dye of formula (1), on the other hand, a composition (B) containing, in a medium which is suitable for dyeing, at least one oxidizing agent and mixing (A) and (B) together immediately before applying this mixture to the keratin-containing fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one dye of formula (1), and, finally, a composition (B) containing, in a medium which is suitable for dyeing, at least one oxidizing agent as defined above, and mixing them together at the time of use immediately before applying this mixture to the keratin-containing fibers.

The composition (A') used according to this second embodiment may optionally be in powder form, the dye(s) of formula (1) (themselves) constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminum oxides, kaolin, talc, silicates, mica and silicas.

An very suitable excipient in the dyeing compositions according to the invention is sawdust.

The powdered composition (A') may also contain binders or coating products in an amount which preferably does not exceed approximately 3% b.w. relative to the total weight of composition (A'). These binders are preferably selected from oils and liquid fatty substances of inorganic, synthetic, animal or plant origin.

Furthermore preferred is a process of dyeing of keratin-containing fibers of the dyes of formula (1) with autooxidable compounds and optionally further dyes.

Furthermore preferred is a process for dyeing keratin-containing fibers with the dyes of formula (1) and capped diazotized compounds, which comprises, a. treating the keratin-containing fibers under alkaline conditions with at least one capped diazotized compound and a coupler compound, and optionally a developer compound and optionally an oxidizing agent, and optionally in the presence of a further dye, and optionally with at least one dye of formula (1); and
b. adjusting the pH in the range of 6 to 2 by treatment with an acid, optionally in the presence of a further dye, and optionally at least one dye of formula (1), with the proviso that at least in one step a. or b. at least one dye of formula (1) is present.

The capped diazotized compound and coupler compound and optionally the oxidizing agent and developer compound can be applied in any desired order successively, or simultaneously.

Preferably, the capped diazotized compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotized compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The following Examples serve to illustrate the present invention. Unless specified otherwise, parts and percentages relate to weight. The amounts of dye specified are relative to the material being colored.

A. Preparation Examples

General Procedure for the Preparation of Distyryl Pyridinium Disulfide Dyes 1 mol equivalent of intermediate

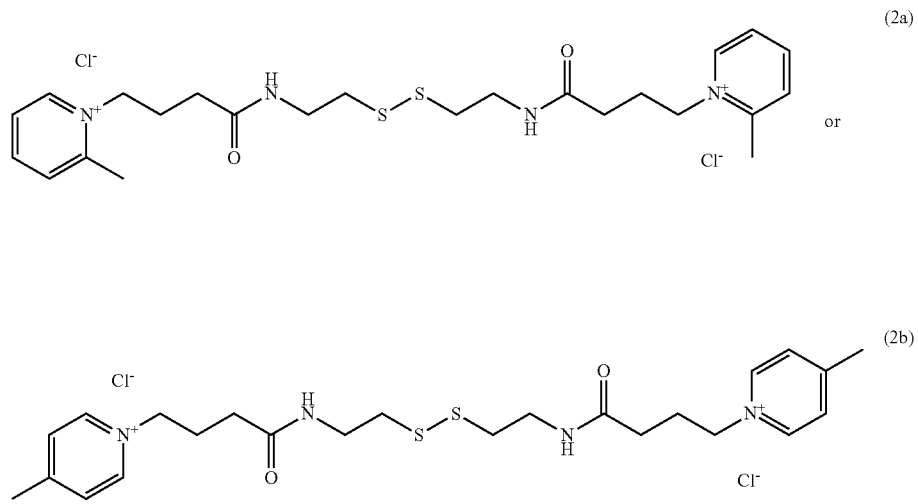

is dissolved in 10 ml of ethanol. Under stirring at 20° C., 2.1 molequivalent of aldehyde is added. 5 molequivalent of pyrrolidine and 5.1 molequivalent of acetic acid is mixed while temperature of the mixture is kept between 0-5° C. The reaction solution is cooled down to 0° C. The pyrrolidine acetate solution is dropwise added, during the solution, the temperature is kept between 0-5° C. The reaction mixture is stirred for 30 minutes at 0-5° C. and another 20 hours at 20° C. When a precipitate formed, the mixture is diluted with a few amount of ethanol, filtered off, washed with acetone and dried. Further purification can be achieved by suspension of the crude material in a mixture of 2-propanol/acetone/ethylacetate (volume ratio 1:1:1). If no precipitate is formed, the reaction mixture is poured into 200 ml of ethylacetate. The precipitate is filtered off, washed with cold ethylacetate and dried in high vacuo.

$^1$H NMR spectra are recorded on a Bruker Avance III/3000; Topspin 3.0.

Example A1 a) Synthesis of N,N-Bis(4-chlorobutyryl)cystamine

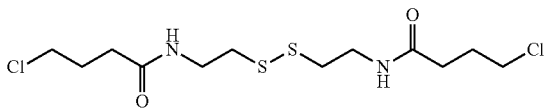 [SMILES: O=C(CCCCl)NCCSSCCNC(=O)CCCCl]

N,N-Bis(4-chlorobutyryl)cystamine was prepared according to literature [J. Org. Chem. 64 (8)(1999) 2903)].

b) 4-(4-methylpyridine-1-ium-1-yl)-N-[2-[2-[4-(4-methylpyridine-1-ium-1-yl)butanoylamino]ethyldisulfanyl]ethyl]butanamide dichloride (intermediate 2b)

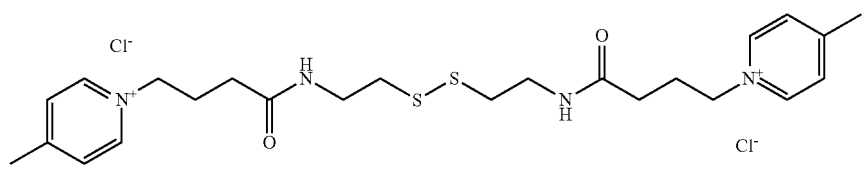

The reaction is performed under a nitrogen atmosphere. 10.0 g (0.0277 mol) N,N -bis(4-chlorobutyryl)cystamine is suspended in 50 ml of tert. amylalcohol. Under stirring, 5.7 g (0.061 mol) 4-picoline is added. The reaction suspension is heated to 105° C. and kept at that temperature for 12 hours. The reaction mixture is cooled down to 20° C. Within 10 minutes 50 ml of ice-cold ethylacetate are added. The reaction mixture is stirred for 30 minutes and poured into 400 ml of ice-cold ethylacetate. The formed suspension is stirred for 10 minutes.

The solvent is decanted and again 200 ml of ice-cold ethylacetate are added. The suspension is stirred for 10 minutes. The precipitate is filtered off and dried in vacuo. Yield: 13 g (87%).

c) 4-[4-[(E)-2-(4-acetamidophenyl)vinyl]pyridine-1-ium-1-yl]-N-[2-[2-[4-[4-[(E)-2-(4-acetamidophenyl)vinyl]pyridine-1-ium-1-yl]butanoylamino]ethyldisulfanyl]ethyl]butanamide dichloride twice with 100 ml ethylacetate and dried in high vacuo at 40° C. Yield: 470 mg, orange solid.

$UV_{vis}$: $\lambda_{max}$=370 nm.

$^1$H NMR (MeOD): δ=1.2 (s; C$\underline{H}_3$CO), 2.2-2.4 (m; br, signals overlapping, CH$_2$), 2.83 (m; CH$_2$), 3.45 (m; CH$_2$), 4.55 (t; NCH$_2$), 7.4 and 7.9 (each dd; C$\underline{H}$=C$\underline{H}$), 8.15 and 8.8 (each m; Aryl-H) ppm.

MS (ESI) $C_{42}H_{50}N_6O_4S_2^{2+}$(767.01), m/z$_{found}$=383.

Example A2

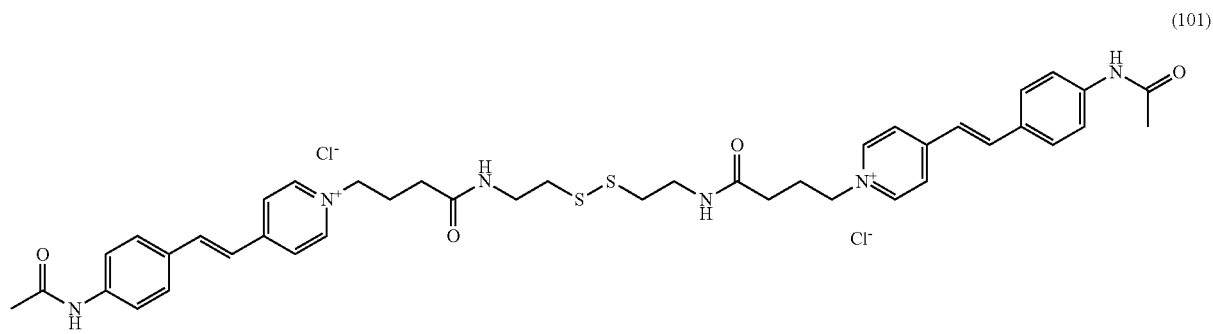 [SMILES: CC(=O)Nc1ccc(/C=C/c2cc[n+](CCCC(=O)NCCSSCCNC(=O)CCC[n+]3ccc(/C=C/c4ccc(NC(C)=O)cc4)cc3)cc2)cc1 ; [Cl-] ; [Cl-]]

(101)

1.5 g (0.0027 mol) of intermediate 2b and 0.9 g (0.002553 mol) 4-acetamidobenzaldehyde are dissolved in 10 ml ethanol. The reaction mixture is stirred and cooled down to 0-5° C. A mixture of 1.6 ml (0.0189 mol) pyrrolidine and 1.1 ml acetic acid (0.0189 mol) is added dropwise. During the addition, the temperature of the reaction mixture is kept between 0-5° C. The reaction mixture is stirred for 30 minutes at 0-5° C. and 20 hours at 20° C. The obtained reaction mixture is poured into 190 ml of 2-propanol. The yellow suspension is stirred for 3 hours at 0-5° C. The formed precipitate is filtered off, washed with 2-propanol, (4-[4-[(E)-2-[4-[2-cyanoethyl(methyl)amino]phenyl]vinyl]pyridine-1-ium-1-yl]-N-[2-[2-[4-[4-[(E)-2-[4-[2-cyanoethyl(methyl)amino]phenyl]vinyl]pyridine-1-ium-1-yl]butanoylamino]ethyl-disulfanyl]ethyl]butanamide dichloride

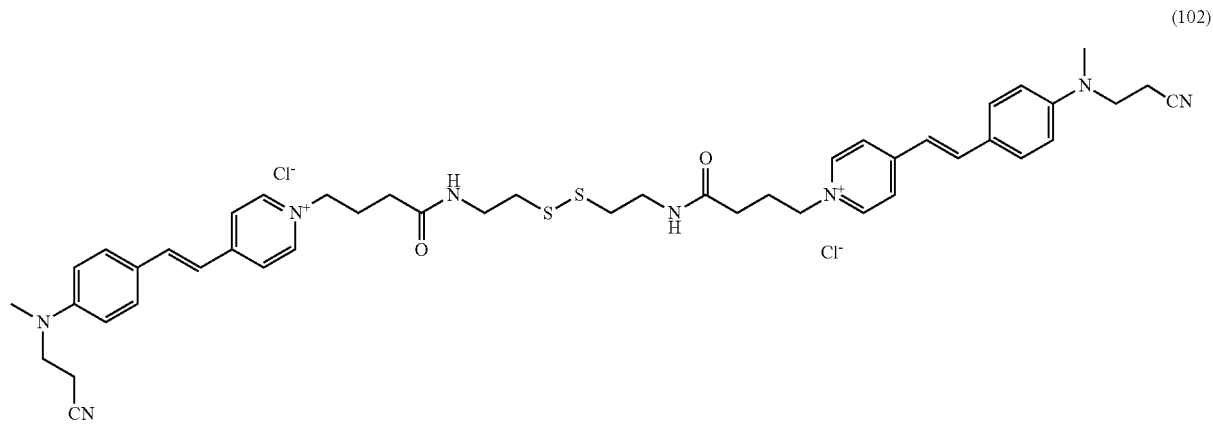 [SMILES: CN(CCC#N)c1ccc(/C=C/c2cc[n+](CCCC(=O)NCCSSCCNC(=O)CCC[n+]3ccc(/C=C/c4ccc(N(C)CCC#N)cc4)cc3)cc2)cc1 ; [Cl-] ; [Cl-]]

(102)

1.5 g (0.0027 mol) of intermediate 2b and 1.04 g (0.00553 mol) 4-cyanoethyl methylamino-benzaldehyde are reacted and worked-up as described in the general procedure. Yield: 860 mg, orange solid.

UV$_{vis}$: $\lambda_{max}$=460 nm.

$^1$H NMR (MeOD): δ=2.0, 2.2-2.4, 2.7-2.9, 3.2 (m; overlapping signals, CH$_2$), 3.80 (m; NCH$_3$), 4.50 (t; NCH$_2$), 6.8-6.9 (m; Aryl-H), 7.1 and 7.8 (each d; CH=CH), 7.6, 8.0 and 8.6 (each m; Aryl-H) ppm.

MS (ESI) C$_{46}$H$_{56}$N$_8$O$_2$S$_2^{2+}$(816.4), m/z$_{found}$=408.

Example A3

4-[4-[(E)-2-(4-pyrazol-1-ylphenyl)vinyl]pyridine-1-ium-1-yl]-N-[2-[2-[4-[4-[(E)-2-(4-pyrazol-1-ylphenyl)vinyl]pyridine-1-ium-1-yl]butanoylamino]ethyldisulfanyl]ethyl]butanamide dichloride

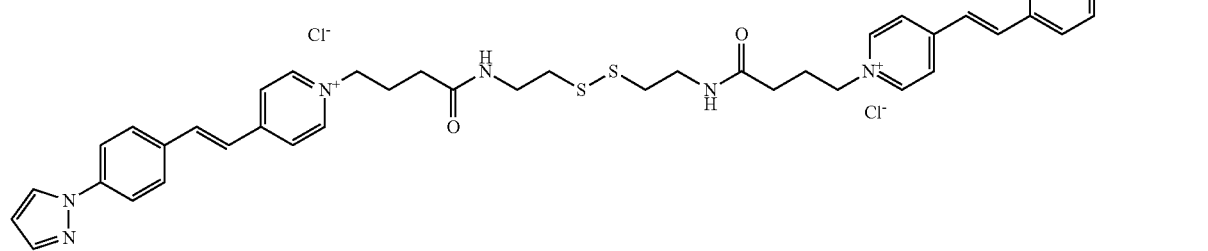

(103)

1.5 g (0.0027 mol) of intermediate 2b and 1.00 (0.00553 mol) 4-(1H-Pyrazol-1yl)benzaldehyde are reacted and worked-up as described in the general procedure.

Yield: 1.28 g, yellow solid.

UV$_{vis}$: $\lambda_{max}$=370 nm.

$^1$H NMR (DMSO-d$_6$): δ=2.19-2.22 (m; CH$_2$), 2.77(t; CH$_2$), 3.29 (m; CH$_2$), 4.55 (t; NCH$_2$), 6.60 (m; Aryl-H); 7.81, 7.90, 7.98 (m; Aryl-H), 7.60 and 8.1 (each d; CH=CH), 8.25 (d; Aryl-H), 8.31 (m; CONH), 8.62 and 8.98(m; Aryl-H) ppm.

Example A4

4l-[4-[(E)-2-(4-methoxyphenyl)vinyl]pyridine-1-ium-1-yl]-N-[2-[2-[4-[4-[(E)-2-(4-methoxy-phenyl)vinyl]pyridine-1-ium-1-yl]butanoylamino]ethyldisulfanyl]ethyl]butanamide dichloride 3.0 g (0.0055 mol) of intermediate (2b) and 1.53 g (0.0113 mol) of 4-methoxy-benzaldehyde are reacted and worked-up as described in the general procedure.

Yield: 1.1 g, yellowish solid.

UV$_{vis}$: $\lambda_{max}$=369 and 385 nm.

$^1$H NMR (DMSO-d$_6$): δ=1.3-1.4 (m; CH$_3$CH$_2$), 2.17 (m; CH$_2$), 2.77 (t, CH$_2$), 3.22 (m; CH$_2$), 4.1 (m; CH$_3$CH$_2$), 4.52 (t; NCH$_2$), 7.11 (d; Aryl -H); 7.37 and 8.00 (each d; CH=CH), 7.70 (m; Aryl-H), 8.18 (d; Aryl-H), 8.37 (t; CONH), 8.93 (d; Aryl-H) ppm.

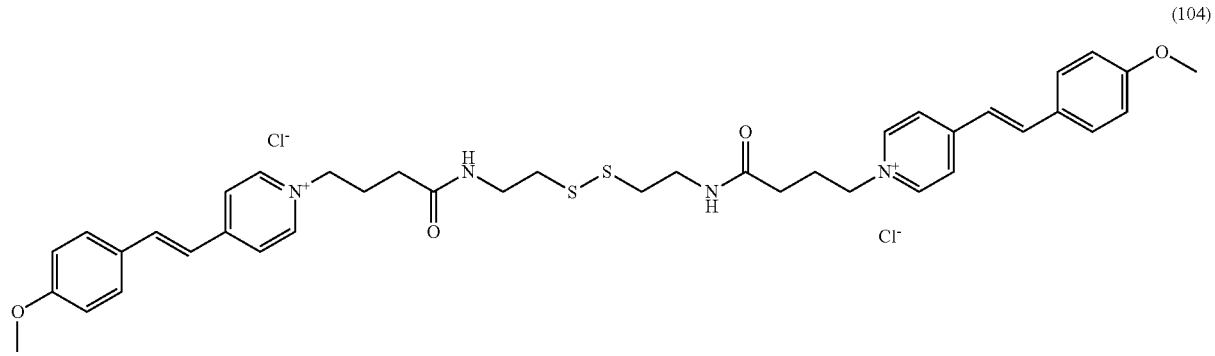 [SMILES: COc1ccc(/C=C/c2cc[n+](CCCC(=O)NCCSSCCNC(=O)CCC[n+]3ccc(/C=C/c4ccc(OC)cc4)cc3)cc2)cc1 ; [Cl-] ; [Cl-]]

(104)

Example A5

4-[4-[(E)-2-(2-methoxyphenyl)vinyl]pyridine-1-ium-1-yl]-N-[2-[2-[4-[4-[(E)-2-(2-methoxy-1-ylphenyl)vinyl]pyridine-1-ium-1-yl]butanoylamino]ethyldisulfanyl]ethyl]butanamide dichloride

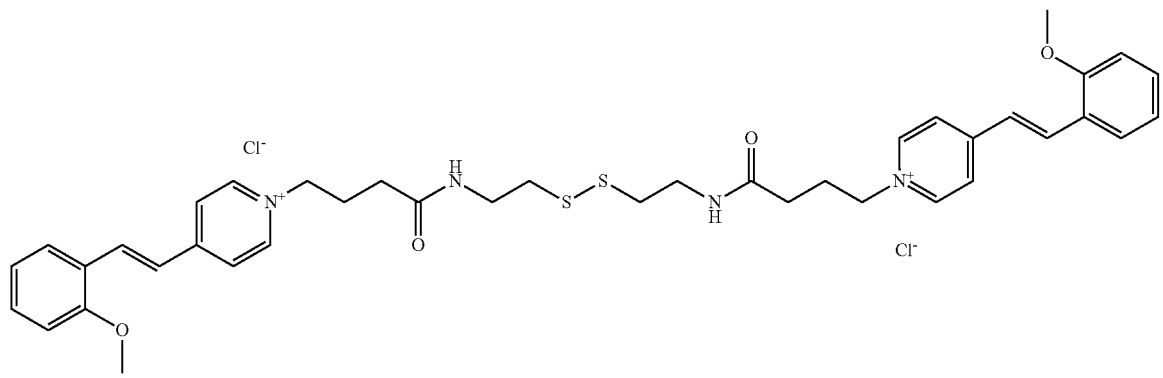

(105)

3.0 g g (0.0055 mol) intermediate 2b and 1.53 g (0.0113 mol) of 2-methoxy-benzaldehyde are reacted and worked-up as described in the general procedure.

Yield: 500 mg, yellowish solid.
$UV_{vis}$: $\lambda_{max}$=370 and 385 nm.
$^1$H NMR (DMSO-$d_6$): δ=2.1-2.2 (m; CH$_2$), 2.76 (m; CH$_2$), 3.30 (m; CH$_2$), 3.90 (s; OCH$_3$), 4.54 (t; NCH$_2$), 7.05 (t; Aryl-H), 7.16 (d; Aryl-H), 7.40 (t; Aryl-H), 7.54 and 8.08 (each d; CH=CH), 7.76 (d; Aryl-H), 8.24 (d; Aryl-H), 8.33 (m; CONH), 8.93 (d, Aryl-H) ppm.

Example A6

4-[4-[(E)-2-(4-ethoxyphenyl)vinyl]pyridine-1-ium-1-yl]-N-[2-[2-[4-[4-[(RE)-2-(4-ethoxyphenyl)vinyl]pyridine-1-ium-1-yl]butanoylamino]ethyldisulfanyl]ethyl]butanamide dichloride

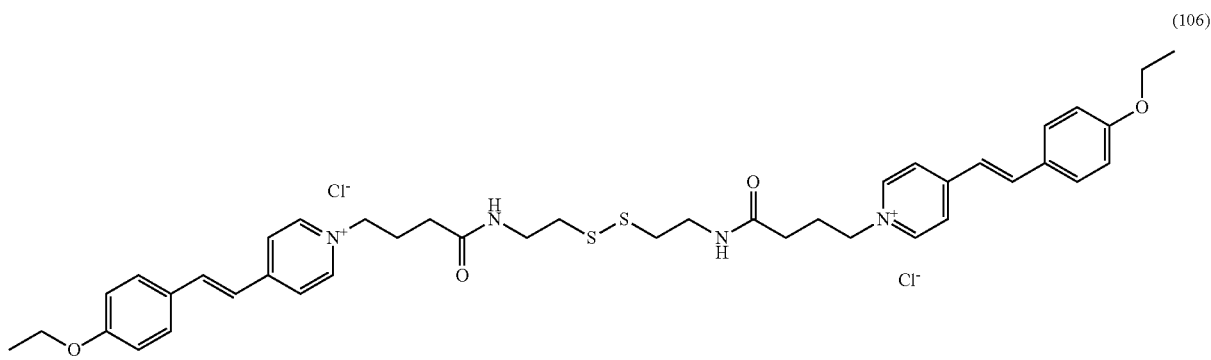 [SMILES: CCOc1ccc(/C=C/c2cc[n+](CCCC(=O)NCCSSCCNC(=O)CCC[n+]3ccc(/C=C/c4ccc(OCC)cc4)cc3)cc2)cc1 ; [Cl-] ; [Cl-]]

(106)

3.0 g (0.0027 mol) intermediate 2b and 1.7 g (0.0113 mol) of 4-ethoxy-benzaldehyde are reacted and worked-up as described in the general procedure.

Yield: 1.1 g, yellow solid.
$UV_{vis}$: $\lambda_{max}$=372 and 385 nm.
$^1$H NMR (DMSO-$d_6$): δ=2.15, 2.76 (each m; CH$_2$), 3.20 (m; overlapping signals, CH$_2$), 3.83 (s; OCH$_3$), 4.51 (t; NCH$_2$), 7.05 (t; Aryl-H), 7.36 and 8.02 (each d; CH=CH), 7.72 (d; Aryl-H), 8.18 (d; Aryl-H), 8.23 (m; CONH), 8.90 (d; A 1-H) ppm.

Example A7

4-[4-[(E)-2-(4-isopropoxyphenyl)vinyl]pyridine-1-ium-1-yl]-N-[2-[2-[4-[4-[(E)-2-(4-isopropoxyphenyl)vinyl]pyridine-1-ium-1-yl]butanoylamino]ethyldisulfanyl]ethyl]butanamide dichloride

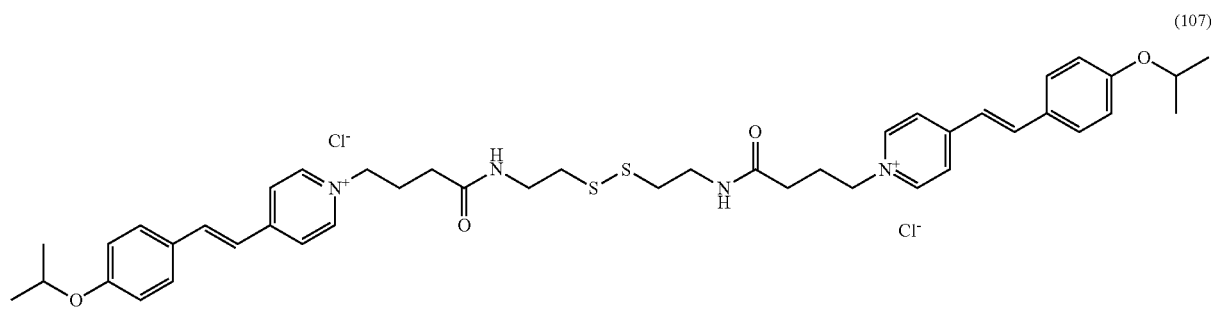 [SMILES: CC(C)Oc1ccc(/C=C/c2cc[n+](CCCC(=O)NCCSSCCNC(=O)CCC[n+]3ccc(/C=C/c4ccc(OC(C)C)cc4)cc3)cc2)cc1 ; [Cl-] ; [Cl-]]

(107)

1.5 g (0.0027 mol) intermediate 2b and 0.91 g (0.00553 mol) of 4-isopropoxy-benzaldehyde are reacted and worked-up as described in the general procedure.

Yield: 1.3 g, yellow powder.

$^1$H NMR (DMSO-d$_6$): δ=1.0-1.4 (each t; C$\underline{H}_3$), 2.0-2.2 (m; CH$_2$), 2.7-2.9 (m; CH$_2$), 3.34 (m; CH$_2$), 4.09 and 4.11 (each q; CH$_3$C$\underline{H}_2$), 4.50 (t; NCH$_2$), 7.05 (d; Aryl-H); 7.36 and 8.00 (each d; C$\underline{H}$=C$\underline{H}$), 8.18 (m; Aryl-H), 8.3 (m; CON$\underline{H}$), 8.90 (d; Aryl-H) ppm.

Example A8

4-[4-[(E)-2-(3,4,5-trimethoxyphenyl)vinyl]pyridine-1-ium -1-yl]-N-[2-[2-[4-[4-[(E)-2-(3,4,5-trimethoxyphenyl)vinyl]pyridine-1-ium-1-yl]butanoylamino]ethyldisulfanyl]ethyl]butanamide dichloride

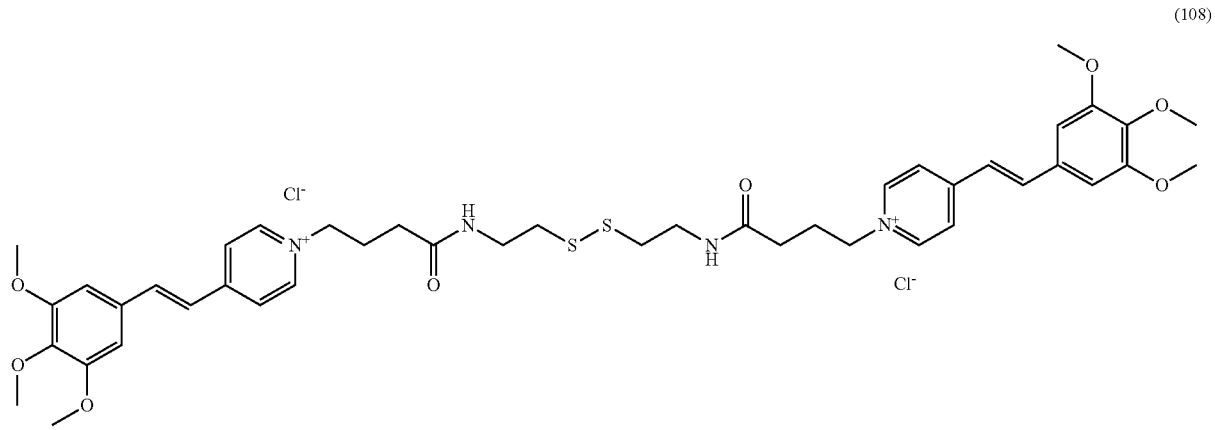 [SMILES: COc1cc(/C=C/c2cc[n+](CCCC(=O)NCCSSCCNC(=O)CCC[n+]3ccc(/C=C/c4cc(OC)c(OC)c(OC)c4)cc3)cc2)cc(OC)c1OC ; [Cl-] ; [Cl-]]

(108)

3.0 g (0.0055 mol) intermediate (2b) and 2.21 g (0.0113 mol) of 3,4,5-trimethoxy-benzaldehyde are reacted and worked-up as described in the general procedure.

Yield: 660 mg, yellow solid.

UV$_{vis}$: λ$_{max}$=363 and 385 nm.

$^1$H NMR (DMSO-d$_6$): δ=2.18, 2.77 and 3.30 (m; CH$_2$), 3.73 and 3.87 (each s; OCH$_3$), 4.53(t; NCH$_2$), 7.11 (s; Aryl-H); 7.54 and 8.00 (each d; C$\underline{H}$=C$\underline{H}$), 8.2 (d; Aryl-H), 8.32 (t; CON$\underline{H}$), 8.96 (d; Aryl-H) ppm.

Example A9

4-[4-[(E)-2-(2,4,6-trimethoxyphenyl)vinyl]pyridine-1-ium-1-yl]-N-[2-[2-[4-[4-[(E)-2-(2,4,6-trimethoxyphenyl)vinyl]pyridine-1-ium-1-yl]butanoylamino]ethyldisulfanyl]ethyl]butanamide dichloride

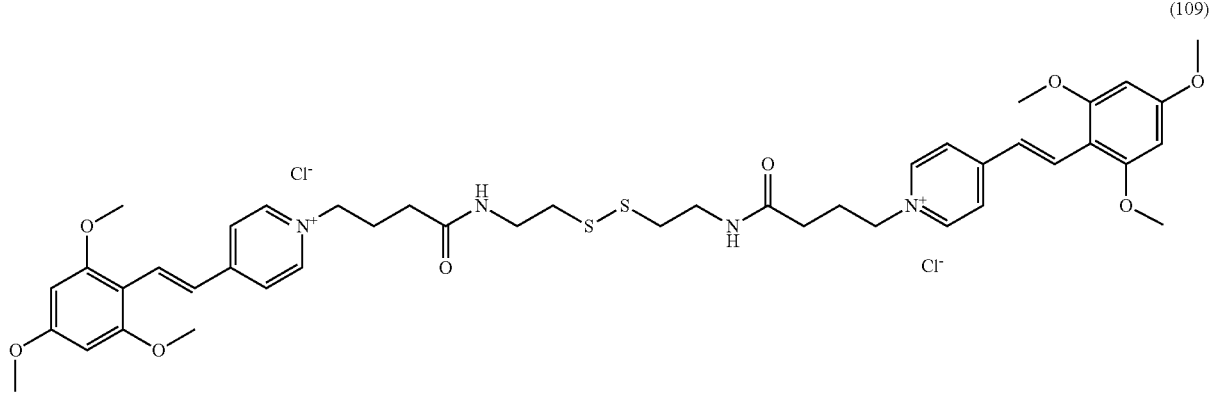 [SMILES: COc1cc(OC)c(/C=C/c2cc[n+](CCCC(=O)NCCSSCCNC(=O)CCC[n+]3ccc(/C=C/c4c(OC)cc(OC)cc4OC)cc3)cc2)c(OC)c1 ; [Cl-] ; [Cl-]]

(109)

A mixture of 6 g (0.011 mol) intermediate 2b and 4.5 g (0.0285 mol) 2,4,6-trimethoxybenzaldehyde is dissolved in 20 ml ethanol and stirred. Within 25 minutes, a cold (T=0-5° C.) solution of 6.3 ml (0.077 mol) pyrrolidine and 4.6 ml (0.080 mol) acetic acid is added portion wise. The reaction mixture is stirred at 20° C. for 20 hours. 40 ml of 2-propanol and afterwards 12 ml ethanolic HCl (1.25 M) are added. The precipitate is filtered off, washed with 2-propanol and dried in vacuo at 40° C. The crude product is recrystallized in water. Yield: 6.5 g (65%), yellow solid.

$UV_{vis}$: $\lambda_{max}$=410 nm,

1H NMR (DMSO-$d_6$): δ=2.11 and 2.15 (m; $CH_2$), 2.76 (t; $CH_2$), 3.30 (m; $CH_2$), 3.87 and 3.92 (each s; $OCH_3$), 4.48 (t; $NCH_2$), 6.33 (s; Aryl-H); 7.54 and 7.97 (each d; C$\underline{H}$=C$\underline{H}$), 8.08 (d; Aryl-H) 8.31 (t; CON$\underline{H}$), 8.86 (d; Aryl-H) ppm.

MS (ESI) $C_{44}H_{66}N_4O_8S_2^{2+}$(832.35), m/$z_{found}$=416

Example A10

4-[4-[(E)-2-(2,4,5-trimethoxyphenyl)vinyl]pyridine-1-ium-1-yl]-N-[2-[2-[4-[4-[(E)-2-(2,4,5-trimethoxyphenyl)vinyl]pyridine-1-ium-1-yl]butanoylamino]ethyldisulfanyl]ethyl]butanamide dichloride

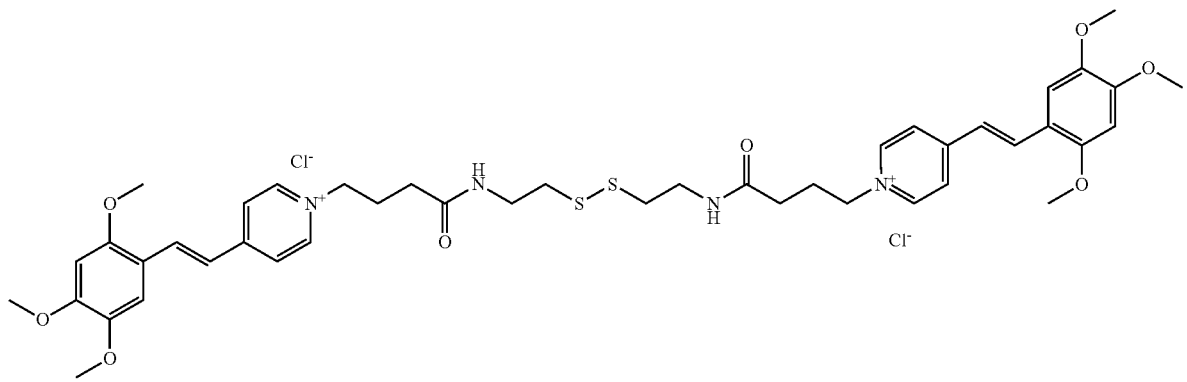

(110)

A mixture of 2.7 g (0.0049 mol) of intermediate 2b and 1.9 g (0.01 mol) 2,4,5-trimethoxy-benzaldehyde in 10 ml ethanol is treated with 1.8 g (0.025 mol) pyrrolidine and 1.5 g (0.0255 mol) acetic acid as described in example 9. The reaction mixture is stirred for 20 hours at 20° C. and diluted with 5 ml ethanol and 10 ml ethyl acetate. In a beaker, the reaction mixture is cooled (10° C.). 100 ml of ethylacetate is added dropwise. The precipitate is filtered off, washed with 30 ml ethylacetate and dried in high vacuo at 20° C.

Yield: 39.1 g (87%), red solid.

$UV_{vis}$: $\lambda_{max}$=427 nm.

$^1$H NMR (DMSO-$d_6$): δ=2.15 (m; $CH_2$), 2.20 (m; $CH_2$), 2.77 (t, $CH_2$), 3.29 (m; $CH_2$), 3.80 (s; $OCH_3$), 3.89 and 3.92 (each s; $OCH_3$), 4.52 (t; $NCH_2$), 6.77 (s; Aryl-H); 7.37 (s; Aryl-H), 7.45 and 8.04 (each d; C$\underline{H}$=C$\underline{H}$), 8.13 (d; Aryl-H), 8.41 (t; CON$\underline{H}$), 8.89 (d; Aryl-H) ppm.

MS (ESI) $C_{44}H_{56}N_{4}O_{8}S_{2}^{2+}$(832.35), m/$z_{found}$=416.16.

Example A11

4-[4-[(E)-2-(2,4-dimethoxyphenyl)vinyl]pyridine-1-ium-1-yl]-N-[2-[2-[4-[4-[(E)-2-(2,4-dimethoxyphenyl)vinyl]pyridine-1-ium-1-yl]butanoylamino]ethyldisulfanyl]ethyl]butanamide dichloride A solution of 1.5 g (0.0027 mol) intermediate 2b in 7 ml ethanol is stirred at 20° C. To this solution, 0.92 g (0.0055 mol) 2,4-dimethoxybenzaldehyde is added. Within 5 minutes, a cooled solution (T=5° C.) of 1.6 ml pyrrolidine and 1.1 ml acetic acid is added. The reaction mixture is stirred for 20 hours at 20° C. and then diluted with 7 ml ethyl acetate. This reaction solution is poured into 300 ml of ethyl acetate. The formed sticky precipitate is isolated by decantation of supernatant solvent. The raw precipitate is treated with 100 ml of acetone and is stirred for 2 hours at 40° C. The resulted yellow precipitate is filtered off, washed with acetone and dried in high vacuo at 50° C.

Yield: 400 mg, yellow solid.

$UV_{vis}$: $\lambda_{max}$=401 nm.

$^1$H NMR (DMSO-$d_6$): δ=2.18 and 2.23 (each m; $CH_2$), 2.78 (t; $CH_2$), 3.29 (m; $CH_2$), 3.79 and 3.87 (s; $OCH_3$), 4.58 (t; $NCH_2$), 6.77 (s; Aryl-H); 7.03 (dd; Aryl-H), 7.08 (d; Aryl-H), 7.38 (d; Aryl-H), 7.63 and 8.05 (each d; C$\underline{H}$=C$\underline{H}$), 8.25 (d, Aryl-H), 8.46 (t; CON$\underline{H}$), 9.01 (d; Aryl-H) ppm.

MS (ESI) $C_{42}H_{52}N_{4}O_{6}S_{2}^{2+}$(772.3), m/$z_{found}$=386.3.

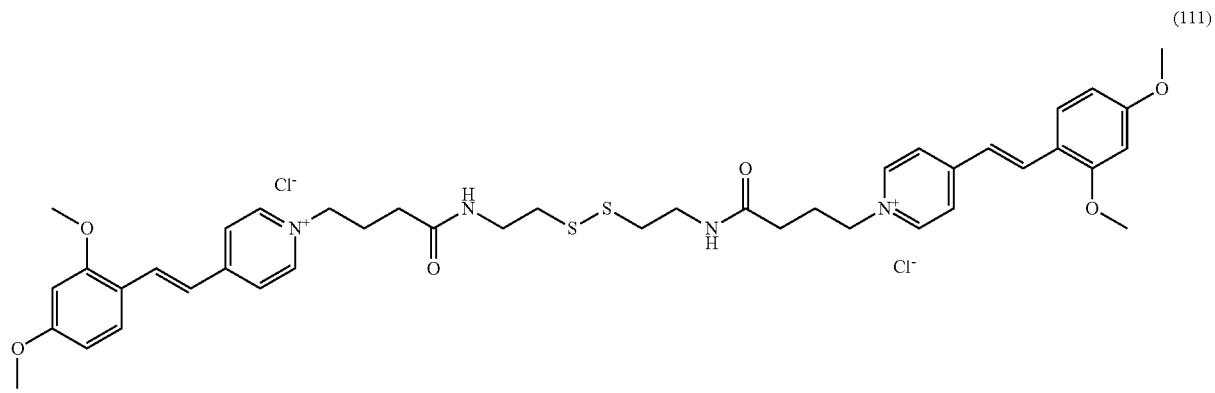 [SMILES: COc1ccc(/C=C/c2cc[n+](CCCC(=O)NCCSSCCNC(=O)CCC[n+]3ccc(/C=C/c4ccc(OC)cc4OC)cc3)cc2)c(OC)c1 ; [Cl-] ; [Cl-]]

(111)

Example A12

4-[4-[(E)-2-(2,3-dimethoxyphenyl)vinyl]pyridine-1-ium-1-yl]-N-[2-[2-[4-l[4-[(E)-2-(2,3-dimethoxyphenyl)vinyl]pyridine-1-ium-1-yl]butanoylamino]ethyldisulfanyl]ethyl]butanamide dichloride 3.0 g (0.0027 mol) of intermediate 2b and 1.87 g (0.0113 mol) of 2,3-dimethoxy-benzaldehyde are reacted and worked-up as described in example 11.

Yield; 400 mg, yellow powder.

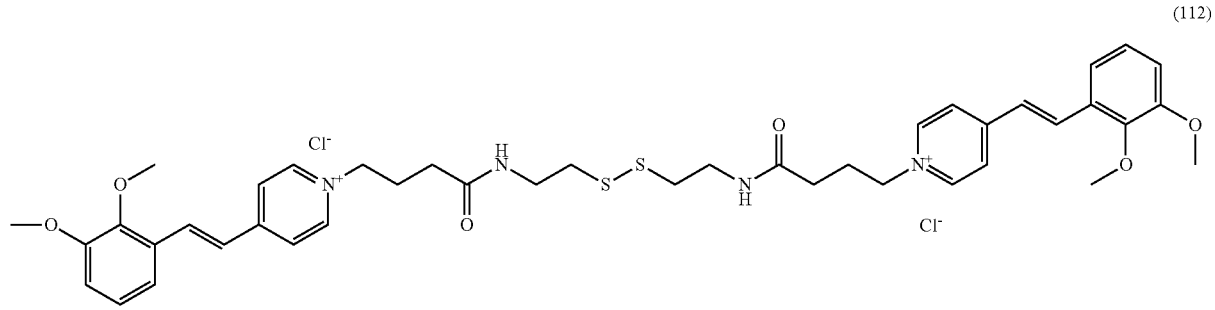

(112)

$^1$H NMR (DMSO-$d_6$): δ=2.19, 2.76, 2.95, 3.36 (each m; CH$_2$), 4.56 (t; NCH$_2$), 7.17 (d; Aryl-H); 7.41 (d; Aryl-H), 7.54 and 8.05 (each d; C$\underline{H}$=C$\underline{H}$), 8.3-8.4 (m; overlapping signals, Aryl-H and CON$\underline{H}$), 8.98 (d; Aryl-H) ppm.

Example A13

4-[4-[(E)-2-(2,5-dimethoxyphenyl)vinyl]pyridine-1-ium-1-yl]-N-[2-[2-[4-[4-[(E)-2-(2,5-dime-thoxyphenyl)vinyl]pyridine-1-ium-1-yl]butanoylamino]ethyldisulfanyl]ethyl]butanamide dichloride

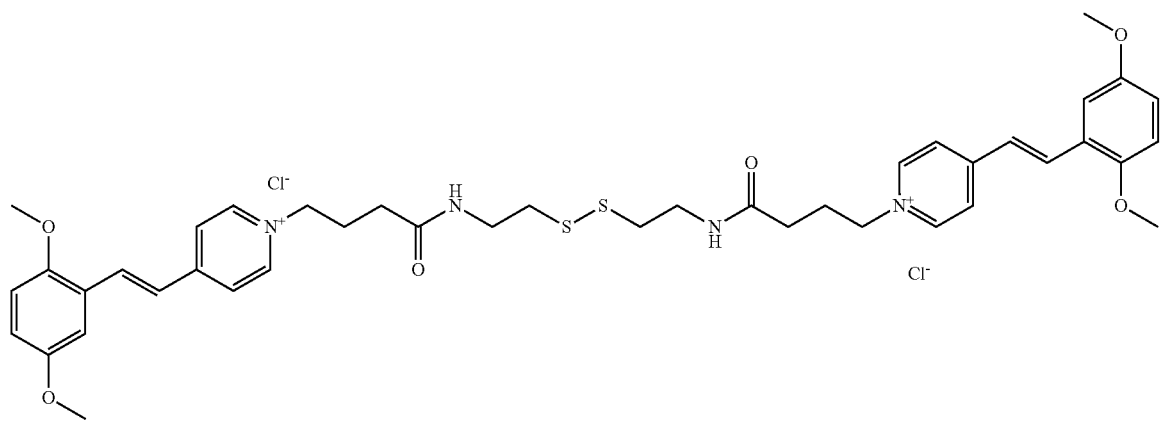

(113)

2.9 g (0.0053 mol) of intermediate 2b and 1.8 g (0.0011 mol) of 2,5-dimethoxy-benzaldehyde are reacted and worked-up as described in the general procedure.

Yield: 2.1 g, yellow solid.

UV$_{vis}$: λ$_{max}$=332 and 401 nm.

$^1$H NMR (DMSO-$d_6$): δ=2.1-2.2 (m; overlapping signals, CH$_2$), 2.77 (t; CH$_2$), 3.37 (m; CH$_2$), 3.87 and 3.92 (s; OCH$_3$), 4.48 (t; NCH$_2$), 6.34 (s; Aryl-H); 7.54 and 8.00 (each d; C$\underline{H}$=C$\underline{H}$), 8.1 (d; Aryl-H), 8.33 (t; CON$\underline{H}$), 8.80 (d; Aryl-H) ppm.

Example A14

4-[4-[(E)-2-(3,4-dimethoxyphenyl)vinyl]pyridine-1-ium-1-yl]-N-[2-[2-[4-[4-[(E)-2-(3,4-di-methoxyphenyl)vinyl]pyridine-1-ium-1-yl]butanoylamino]ethyldisulfanyl]ethyl]butanamide dichloride

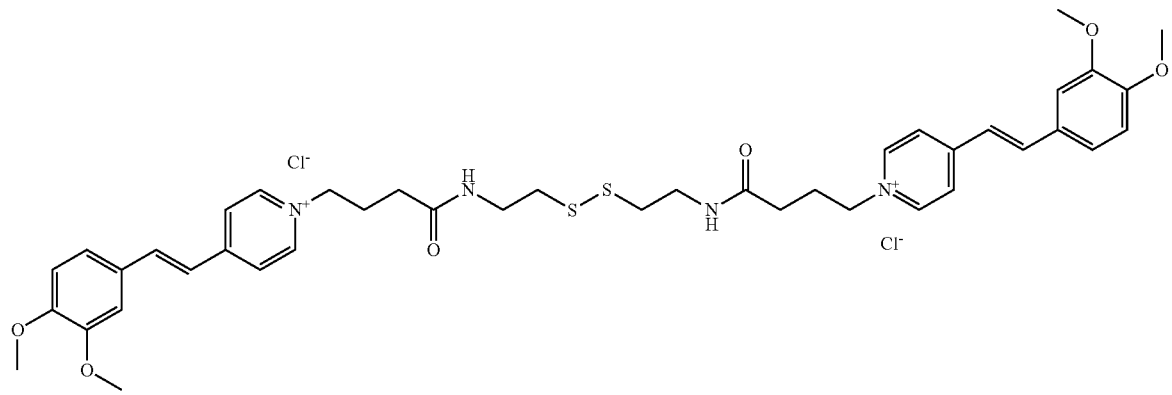

(114)

3.0 g (0.0055 mol) intermediate 2b and 2.19 g (0.0113 mol) 3,4-dimethoxybenzaldehyde are reacted and worked-up as described in the general procedure.

Yield: 1.6 g, yellow solid.

$UV_{vis}$: $\lambda_{max}$=385 nm.

$^1$H NMR (DMSO-d$_6$): δ=2.18, 2.75 (each m; CH$_2$), 3.30 (m; overlapping signals, CH$_2$), 3.83 and 3.86 (each s; OCH$_3$), 4.50 (t; NCH$_2$), 7.07 and 7.30 (each m; Aryl-H), 7.40 and 8.00 (each d; CH=CH), 7.35 (m; Aryl-H), 8.1-8.3 (br m; overlapping, Aryl-H and CONH), 8.89 (d; Aryl-H) ppm.

MS (ESI) $C_{42}H_{52}N_4O_6S_2^{2+}$(773.0), m/z$_{found}$=386.

Example A15

4-[4-[(E)-2-(2,4-diethoxyphenyl)vinyl]pyridine-1-ium-1-yl]-N-[2-[2-[4-[4-[(E)-2-(2,4-diethoxy-phenyl)vinyl]pyridine-1-ium-1-yl]butanoylamino]ethyldisulfanyl]ethyl]butanamide dichloride

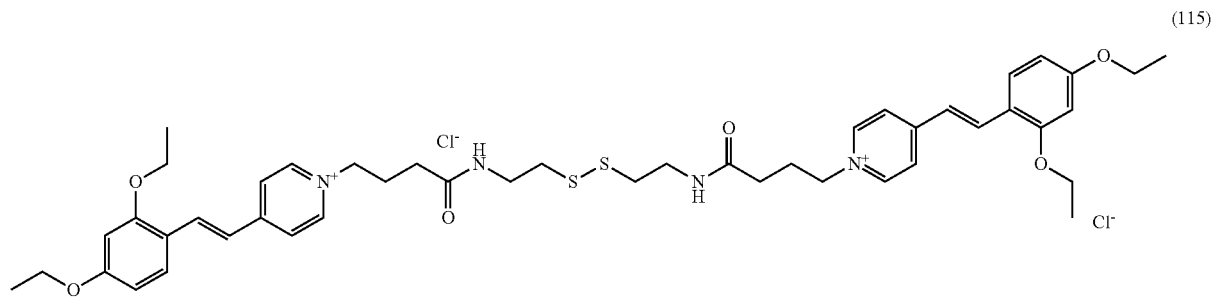 [SMILES: CCOc1ccc(/C=C/c2cc[n+](CCCC(=O)NCCSSCCNC(=O)CCC[n+]3ccc(/C=C/c4ccc(OCC)cc4OCC)cc3)cc2)c(OCC)c1 ; [Cl-] ; [Cl-]]

(115)

1.5 g 0.0027 mol) of intermediate (2b) and 1.07 g (0.00553 mol) 2,4-diethoxybenzaldehyde are reacted and worked-up as described in the general procedure.

Yield: 750 mg, yellow solid.

$\lambda_{max}$=403 nm.

$^1$H NMR (DMSO-d$_6$): δ=1.3-1.4 (m; each H, CH$_3$CH$_2$), 2.0-2.2 (br m; CH$_2$), 2.75 (m; CH$_2$), 3.20 (m; CH$_2$ overlapping), 4.00 and 4.2 (each m; CH$_3$CH$_2$), 4.50 (t; NCH$_2$), 6.6 (d; Aryl-H), 7.7-7.8 (m; overlapping signals, Aryl-H), 7.4 and 8.00 (each dd; CH=CH), 8.30-8.50 (br m; overlapping signals, Aryl-H and CONH), 8.9-9.0 (d; Aryl-H) ppm.

Example A16

4-[4-[(E)-2-(3,4-diethoxyphenyl)vinyl]pyridine-1-ium-1-yl]-N-[2-[2-[4-[4-[(E)-2-(3,4-diethoxy-phenyl)vinyl]pyridine-1-ium-1-yl]butanoylamino]ethyldisulfanyl]ethyl]butanamide dichloride

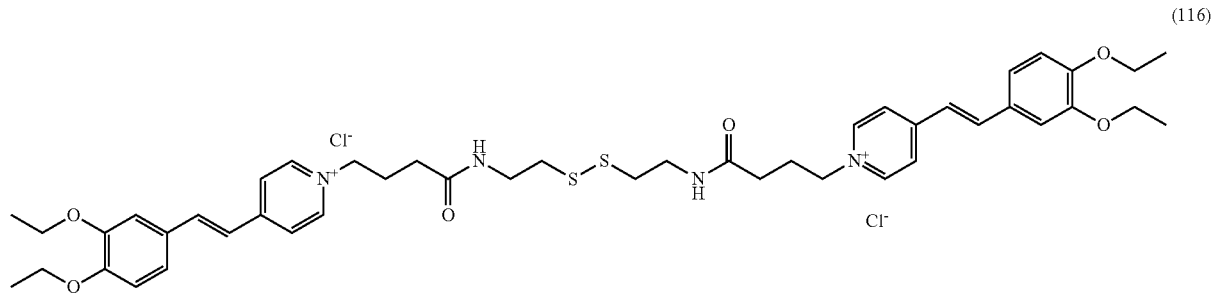 [SMILES: CCOc1ccc(/C=C/c2cc[n+](CCCC(=O)NCCSSCCNC(=O)CCC[n+]3ccc(/C=C/c4ccc(OCC)c(OCC)c4)cc3)cc2)cc1OCC ; [Cl-] ; [Cl-]]

(116)

A solution of 3 g (0.0055 mol) of intermediate 2b and 2.19 g (0.0113 mol) 3,4-diethoxybenzaldehyde in 15 ml ethanol is stirred at 20° C. for 15 minutes. The reaction is cooled to 0-5° C. and a freshly prepared solution of 2.67 g (2.3 ml, 0.0375 mol) pyrrolidine and 2.25 g (2.2 ml, 0.0375 mol) acetic acid is added dropwise while the temperature of the mixture is kept between 0-5° C. The reaction mixture is stirred at 20° C. for 22 hours. The obtained suspension is cooled to 0° C. and the precipitate is filtered off, washed and dried.

Yield; 1.6 g, yellow solid.

$UV_{vis}$: $\lambda_{max}$=395 nm.

$^1$H NMR (DMSO-d$_6$): δ=1.35 and 1.37 (each t; C$\underline{H}_3$CH$_2$), 2.17 (m; CH$_2$), 2.22 (m; CH$_2$), 2.77 (t; CH$_2$), 3.29 (m; CH$_2$), 4.09 and 4.11 (each q; CH$_3$C$\underline{H}_2$), 4.54 (t; NCH$_2$), 7.05 (d; Aryl-H); 7.28 (dd, Aryl-H), 7.41 (d; Aryl-H), 7.45 and 8.00 (each d; C$\underline{H}$=C$\underline{H}$), 8.19 (d; Aryl-H), 8.47 (t; CON$\underline{H}$), 8.89 (d; Aryl-H) ppm.

MS (ESI) $C_{46}H_{60}N_4O_6S_2^{2+}$(828.4), m/z$_{found}$=414.19.

Example 17

4-[4-[(E)-2-(9-ethylcarbazol-3-yl)vinyl]pyridine-1-ium-1-yl]-N-[2-[2-[4-[4-[(E)-2-(9-ethylcarbazol-3-yl)vinyl]pyridine-1-ium-1-yl]butanoylamino]ethyldisulfanyl]ethyl]butanamide dichloride A stirred solution of 3 g of intermediate 2b and 2.53 g (0.01134 mol) 9-ethyl-3-carbazolecarboxyaldehyde is cooled down to 0-5° C. Within 5 minutes, a freshly prepared solution of 3.2 ml pyrrolidine and 2.2 ml acetic acid is added dropwise. The reaction mixture is heated up to 40° C. and stirred for 4 hours at this temperature. The reaction is stirred another 12 hours at 20° C. The orange suspension is filtered off and washed with 2-propanol. The crude product is suspended in 30 ml of cold acetone, stirred for 30 minutes, filtered off and dried in high vacuo at 40° C.

Yield 1.66 g, orange solid.

$UV_{vis}$: $\lambda_{max}$=430 nm.

$^1$H NMR (DMSO-d$_6$): δ=1.3 (m; CH$_3$), 1.6, 2.1-2.2, 2.7-2.9, 3.3 (each m; CH$_2$), 4.49 (m; NCH$_2$), 7.3 (t; Aryl-H); 7.55 (d; Aryl-H), 7.56 and 8.20 (each m; overlapping signals, C$\underline{H}$=C$\underline{H}$), 7.8 (d; Aryl-H), 8.2 (m; overlapping, Aryl-H), 8.3 (m; CON$\underline{H}$), 8.6 (m; Aryl-H), 8.92 (d; Aryl-H) ppm.

MS (ESI) $C_{54}H_{58}N_6O_2S_2^{2+}$(887.2), m/z$_{found}$=443.

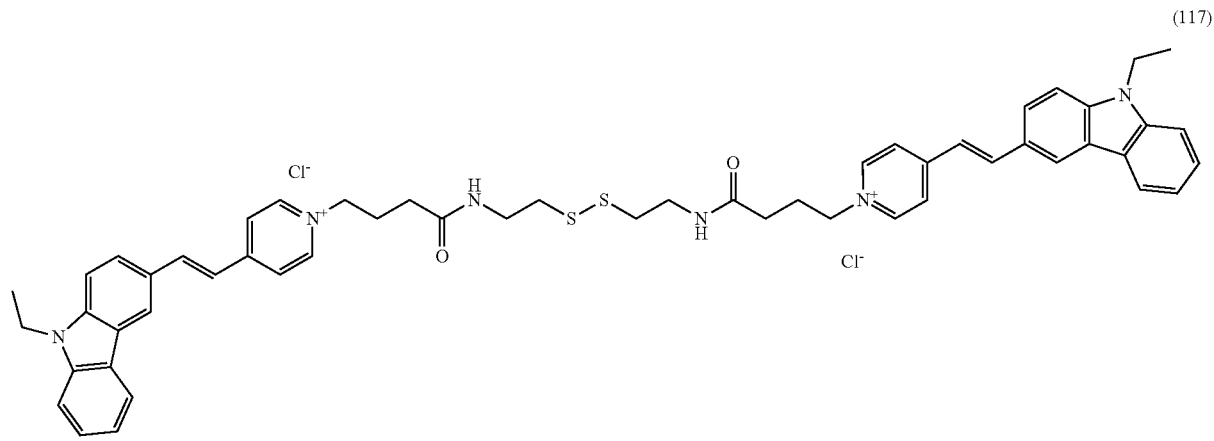 [SMILES: CCn1c2ccccc2c2cc(/C=C/c3cc[n+](CCCC(=O)NCCSSCCNC(=O)CCC[n+]4ccc(/C=C/c5ccc6c(c5)c5ccccc5n6CC)cc4)cc3)ccc21 ; [Cl-] ; [Cl-]]

(117)

Example A18

4-[2-[(E)-2-(3,4-dimethoxyphenyl)vinyl]pyridine-1-ium-1-yl]-N-[2-[2-[4-[2-[(E)-2-(3,4-dimethoxyphenyl)vinyl]pyridine-1-ium-1-yl]butanoylamino]ethyldisulfanyl]ethyl]butanamide dichloride

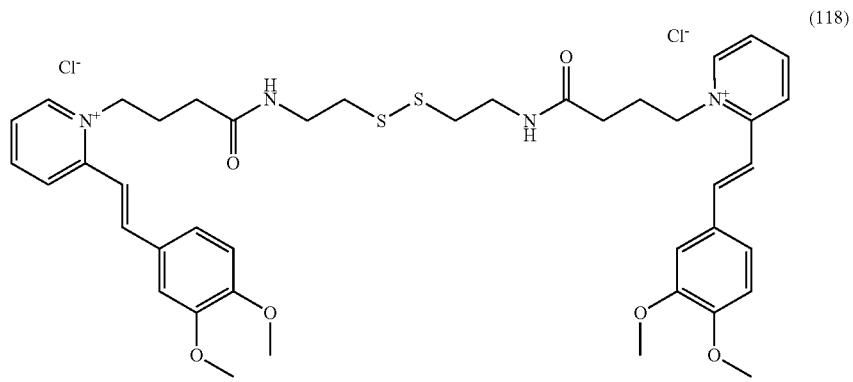 [SMILES: [Cl-] ; COc1ccc(/C=C/c2cccc[n+]2CCCC(=O)NCCSSCCNC(=O)CCC[n+]2ccccc2/C=C/c2ccc(OC)c(OC)c2)cc1OC ; [Cl-]]
(118)

a) 4-(2-methylpyridine-1-ium-1-yl)-N-[2-[2-[4-(2-methylpyridine-1-ium-1-yl)butanoylamino]-ethyldisulfanyl]ethyl]butanamide dichloride (intermediate 2a)

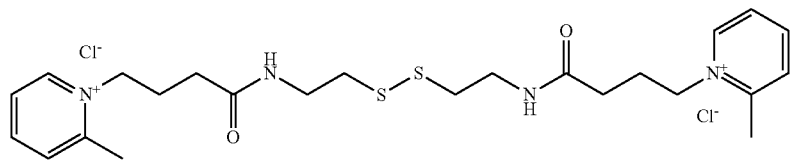 [SMILES: Cc1cccc[n+]1CCCC(=O)NCCSSCCNC(=O)CCC[n+]1ccccc1C ; [Cl-] ; [Cl-]]

The reaction is performed under a nitrogen atmosphere. 5 grams (0.0138 mol) of N,N-bis(4-chlorobutyryl)cystamine (preparation described in example A1a) are suspended in 25 ml (0.238 mol) 2-picoline. The reaction mixture is heated to 90° C. and kept at that temperature for 20 hours. The reaction mixture is cooled to 60° C. and 70 ml acetone is added dropwise within 10 minutes. Then reaction mixture is cooled to 20° C. and poured into 250 ml of ethyl acetate. The formed precipitate is filtered off. The raw product is suspended in 150 ml acetone and poured into 150 ml of ethyl acetate. The formed precipitate is filtered off and dried in vacuo.

Yield: 6.2 g, yellow oil.

b) 4-[2-[(E)-2-(3,4-dimethoxyphenyl)vinyl]pyridine-1-ium-1-yl]-N-[2-[2-[4-[4-[(E)-2-(3,4-dimethoxyphenyl)vinyl]pyridine-1-ium-1-yl]butanoylamino]ethyldisulfanyl]ethyl]butanamide dichloride A reaction mixture of 2.0 g (0.0027 mol) intermediate 2a and 1.25 g (0.0075 mol) 3,4-dimethoxybenzaldehyde is cooled to 0-5° C. Within 5 minutes, a mixture of freshly prepared 2.1 ml pyrrolidine and 1.5 ml acetic acid is added. During the addition, the temperature of the reaction mixture is kept between 0-5° C. The reaction mixture is stirred at 0-5° C. for another 30 minutes and then 20 hours at 20° C. The reaction mixture is diluted with 15 ml of 2-propanol. The formed precipitate is filtered off, washed with 30 ml of 2-propanol and dried in high vacuo at 50° C.

Yield: 1.2 g, yellow solid.

$UV_{vis}$: $\lambda_{max}$=380 nm.

$^1$H NMR (DMSO-$d_6$): δ=2.1, 2.36, 2.79 (each m; $CH_2$), 3.82 and 3.92 (each q; $CH_3CH_2$), 4.67 (m; $NCH_2$), 7.05 (d; Aryl-H); 7.39 (d; Aryl-H), 7.6 and 8.00 (each d; C$\underline{H}$=C$\underline{H}$), 7.6-7.9 (m; overlapping signals, Aryl-H), 8.35-8.55 (m; overlapping signals, Aryl-H and CON$\underline{H}$), 8.92 (d; Aryl-H) ppm.

Example A19

4-[2-[(E)-2-C2,3,4-trimethoxyphenyl)vinyl]pyridine-1-ium-1-yl]-N-[2-[2-[4-[2-[(E)-2-(3,4,5-trimethoxyphenyl)vinyl]pyridine-1-ium-1-yl]butanoylamino] ethyldisulfanyl]ethyl]butanamide dichloride

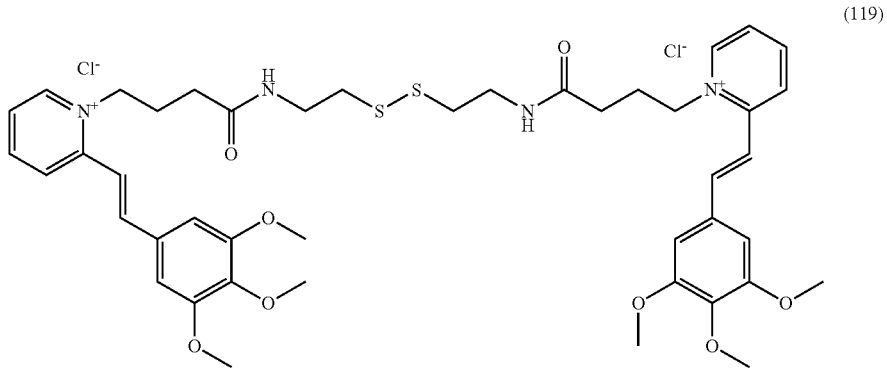 [SMILES: COc1cc(/C=C/c2cccc[n+]2CCCC(=O)NCCSSCCNC(=O)CCC[n+]2ccccc2/C=C/c2cc(OC)c(OC)c(OC)c2)cc(OC)c1OC ; [Cl-] ; [Cl-]]

(119)

A reaction mixture of 1.6 g (0.00292 mol) of intermediate 2a and 1.20 g (0.0075 mol) 3,4,5-trimethoxybenzaldehyde in 12 ml ethanol is reacted and worked-up as described for example A18b.

Yield: 800 mg, yellow solid,
$UV_{vis}$: $\lambda_{max}$=362 nm.
$^1H$ NMR (MeOD): δ=2.22, 2.53, 2.82, 3.5 (each m; $CH_2$), 3.78 and 3.97 (each s; $OCH_3$), 4.66 (t; $NCH_2$), 7.25 (s; Aryl-H); 7.7 and 8.5 (each d; C$\underline{H}$=C$\underline{H}$), 7.7-7.9 (m; overlapping signals, Aryl-H), 8.46 and 8.80 (d; Aryl-H) ppm.

Example A20

4-[2-[(E)-2-[4-[2-cyanoethyl(methyl)amino]phenyl] vinyl]pyridine-1-ium-1-yl]-N-[2-[2-[4-[2-[(E) -2-[4-[2-cyanoethyl(methy)amino]phenyl]vinyl]pyridine-1-ium-1-yl]butanoylamino]ethyldisulfanyl]ethyl] butanamide dichloride

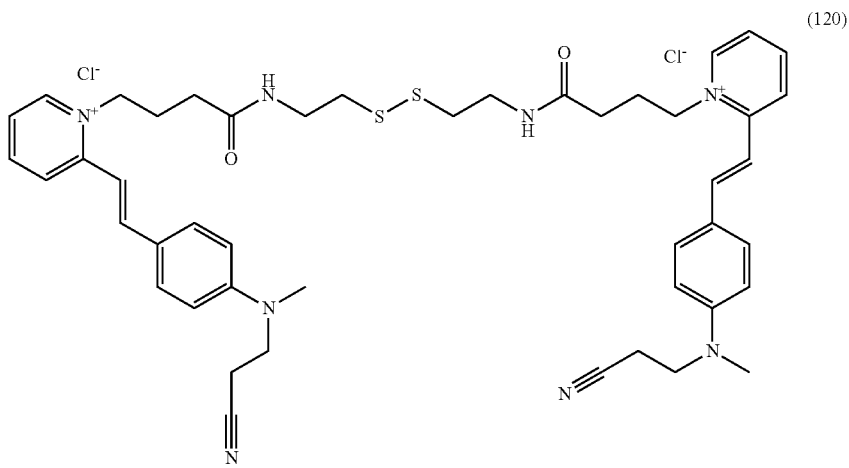 [SMILES: CN(CCC#N)c1ccc(/C=C/c2cccc[n+]2CCCC(=O)NCCSSCCNC(=O)CCC[n+]2ccccc2/C=C/c2ccc(N(C)CCC#N)cc2)cc1 ; [Cl-] ; [Cl-]]

(120)

A reaction mixture of 1.6 g (0.00292 mol) of intermediate 2a and 1.12 g (0.00598 mol) 4-cyanoethyl-methylaminobenzaldehyde in 12 ml ethanol is reacted and worked-up as described for example A18b.

Yield: 730 mg, yellow-orange solid.

UV$_{vis}$: $\lambda_{max}$=433 nm.

$^1$H NMR (DMSO-d$_6$): δ=2.0, 2.3-2.4, 2.7-2.9, 3.3 (m; broad signals, overlapping, CH$_2$), 3.80 (m; NCH$_3$), 4.70 (t; NCH$_2$), 6.9 (m; Aryl-H), 7.45 and 7.95 (each d; C$\underline{H}$=C$\underline{H}$), 8.4 (m; CON$\underline{H}$), 8.5 and 8.80 (each m; Aryl-H) ppm.

Example A21

4-[2-[(E)-2-(4-acetamidophenyl)vinyl]pyridine-1-ium-1-yl]-N-[2-[2-[4-[2-[(E)-2-(4-acetamido-phenyl)vinyl]pyridine-1-ium-1-yl]butanoylamino]ethyldisulfanyl]ethyl]butanamide dichloride

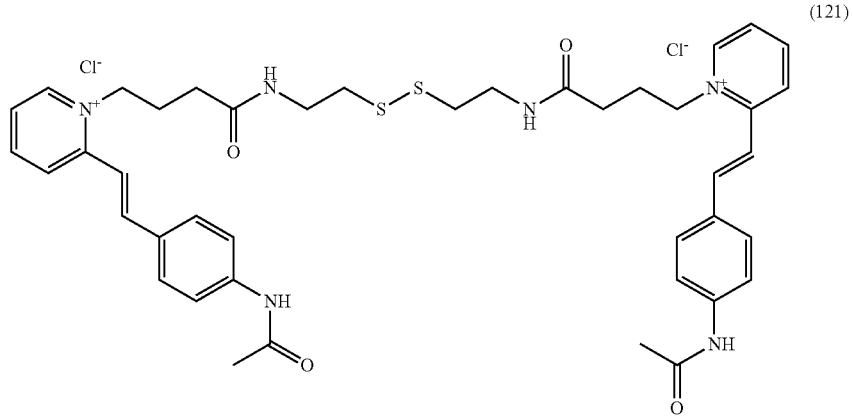 [SMILES: CC(=O)Nc1ccc(/C=C/c2cccc[n+]2CCCC(=O)NCCSSCCNC(=O)CCC[n+]2ccccc2/C=C/c2ccc(NC(C)=O)cc2)cc1 ; [Cl-] ; [Cl-]]

(121)

A reaction mixture of 3.0 g (0.0055 mol) of intermediate 2a and 1.84 g (0.0113 mol) 4-acetamidobenzaldehyde in 12 ml ethanol is reacted and worked-up as described for example A18b.

Yield: 600 mg, yellow solid.

$^1$H NMR (DMSO-d$_6$): δ=2.05, 2.28 (m; CH$_2$), 2.78 (m; CH$_2$), 3.45 (m; CH$_2$), 4.70 (m; NCH$_2$), 7.06 (m; Aryl-H), 7.6 and 8.0 (each dd; C$\underline{H}$=C$\underline{H}$), 8.3-8.5 (each m; overlapping signals; Aryl-H and CON$\underline{H}$), 8.92 (d, Aryl-H) ppm.

Example A22

4-[2-[(E)-2-(4-methexyphenyl)vinyl]pyridine-1-ium-1-yl]-N-[2-[2-[4-[2-[(E)-2-(4-methoxy-phenyl)vinyl]pyridine-1-ium-1-yl]butanoylamino]ethyldisulfanyl]ethyl]butanamide dichloride

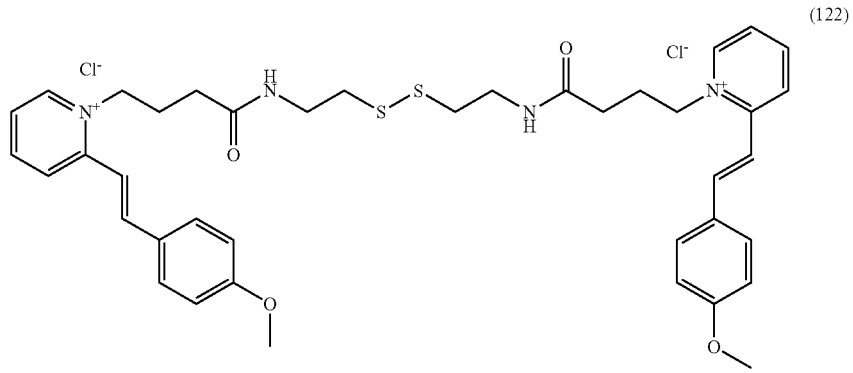 [SMILES: COc1ccc(/C=C/c2cccc[n+]2CCCC(=O)NCCSSCCNC(=O)CCC[n+]2ccccc2/C=C/c2ccc(OC)cc2)cc1 ; [Cl-] ; [Cl-]]

(122)

A reaction mixture of 3.0 g (0.0055 mol) intermediate 2a and 1.53 g (0.0113 mol) 4-methoxy-benzaldehyde in 12 ml ethanol is reacted and worked-up as described for example A18b.

Yield: 900 mg, weak yellow solid.

$UV_{vis}$: $\lambda_{max}$=370 nm.

$^1$H NMR (DMSO-d$_6$): δ=2.05, 2.35, 2.75 (m; CH$_2$), 3.3-3.4 (m; overlapping signals, CH$_2$), 3.83 (s; OC$\underline{H}_3$), 4.72 (t; NCH$_2$), 7.05 (d; Aryl-H); 7.62 and 7.95 (each d; C$\underline{H}$=C$\underline{H}$), 7.8-8.0 (m; overlapping signals, Aryl-H), 8.40 (t; CON$\underline{H}$), 8.4-8.6 (each m; Aryl-H), 8.92 (d; Aryl -H) ppm.

Example A23

4-[2-[(E)-2-(2-methoxyphenyl)vinyl]pyridine-1-ium-1-yl]-N-[2-[2-[4-[2-[(E)-2-(2-methoxy-phenyl)vinyl] pyridine-1-ium-1-yl]butanoylamino]ethyldisulfanyl] ethyl]butanamide dichloride (123)

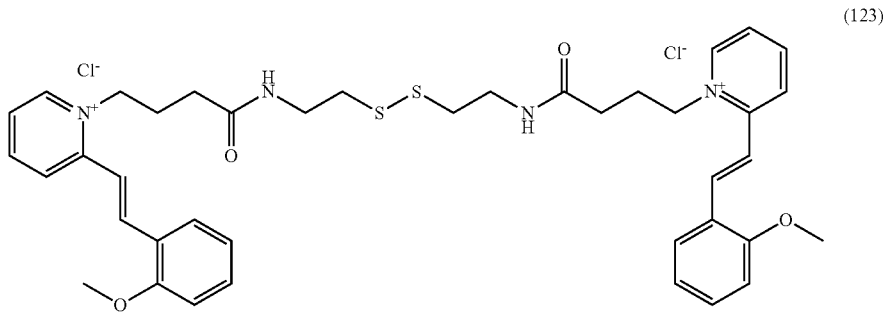 [SMILES: COc1ccccc1/C=C/c1cccc[n+]1CCCC(=O)NCCSSCCNC(=O)CCC[n+]1ccccc1/C=C/c1ccccc1OC ; [Cl-] ; [Cl-]]

A reaction mixture of 3.0 g (0.0055 mol) intermediate 2a and 1.53 g (0.0113 mol) 2-methoxybenzaldehyde in 12 ml ethanol is reacted and worked-up as described for example A18b.

Yield: 900 mg, weak yellow solid.

$UV_{vis}$: $\lambda_{max}$=363 nm.

$^1$H NMR (DMSO-d$_6$): δ=2.0-2.1, 2.33, 2.76 (each m; CH$_2$), 3.26 (m; CH$_2$), 3.92 (s; OC$\underline{H}_3$), 4.75(t NCH$_2$), 7.05 (t; Aryl-H), 7.15 (d; Aryl-H); 7.45 (t; Aryl-H), 7.75 and 8.1 (each d; C$\underline{H}$=C$\underline{H}$), 7.9-8.1 (m; overlapping signals. Aryl-H), 8.46 (m; CONH), 8.4-8.6 (each m, overlapping signals, A l-H), 9.00 (d; Aryl-H) ppm.

Example A24

4-[(E)-2-(3,4-diethoxyphenyl)vinyl]-1-[2-[2-[4-[(E)-2-(3,4-diethoxyphenyl)vinyl]pyridine-1-ium-1-yl] ethyldisulfanyl]ethyl]pyridine-1-ium; methanesulfonate (124)

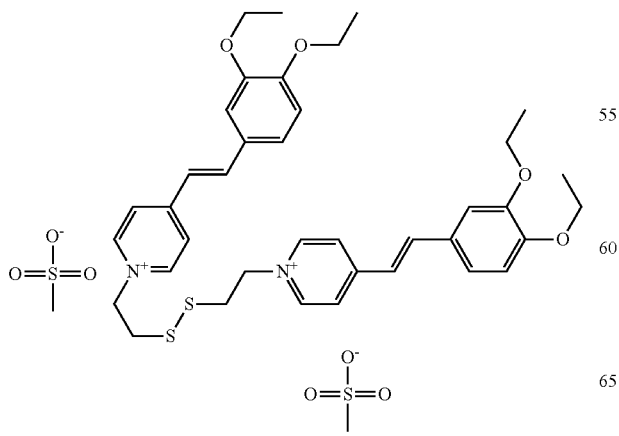

a)

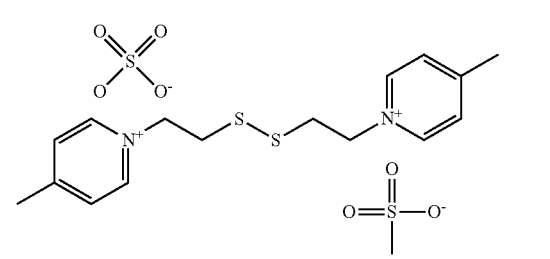

57.2 g (454 mmol) dithioethanol and 105.3 ml (1361 mmol) mesylchloride are treated and worked-up as described in WO2007/003506.

Yield: 115 g, colorless solid.

b)

Intermediate 3b

A solution of 0.93 g (3.0 mmol) of the crude dimesylate intermediate prepared in a) in 10 ml methylimidazole is stirred at 20° C. To this solution, 9.7 ml (100 mmol) of 4-picoline is added. The reaction mixture is heated up to 70° C. and stirred for 16 hours. Afterwards, the reaction solution is cooled to 20° C. and 50 ml ethyl acetate is added. The reaction solution is allowed to stand for 1 hour. The formed oily precipitate is separated from the supernatant solution by decantation. The precipitate is suspended in 5 ml methanol and another 50 ml acetate are added. The formed precipitate is separated by decantation. The crude product is dried at high vacuo at 20° C. and directly used for the next step.

c) A reaction mixture of 1.5 g (3.0 mmol) of the 4-picoline intermediate prepared in example 24b) in 50 ml methanol is stirred at 0° C. Then, 1.7 ml (21 mmol) pyrrolidine, 1.3 ml (22.4 mmol) glacial acetic acid and 1.75 g (9.0 mmol) of 3,4-diethoxybenzaldehyde is added. The reaction solution is stirred for 2 hours at 0° C. Than the solution is allowed to reach 22° C. and stirred at this temperature for further 16 hours. 30 ml of a mixture ethyl acetate/tert.butyl methyl ether (1:1 v/v) is added. The reaction mixture is cooled down to −10° C. and kept there for 15 hours. The formed precipitate is filtered off, washed with 40 ml of acetone and dried in high vacuo at 20° C.

Yield: 700 mg, yellow solid.
$UV_{vis}$: $\lambda_{max}$=402 nm.
$^1$H NMR (DMSO-d$_6$): δ=2.4 (s; CH$_3$S), 3.4 (m; C$\underline{H}_2$), 4.15 (m; OCH$_2$), 4.75 (m; NCH$_2$), 7.1 (d; Aryl-H); 7.30 (dd; Aryl-H), 7.4 and 8.00 (each d; C$\underline{H}$=C$\underline{H}$), 8.25 and 8.9 (m; overlapping signals, Aryl-H), 8.35-8.55 (m; overlapping signals, Aryl-H and CON$\underline{H}$), 8.92 (each d; Aryl-H) ppm.
MS (ESI) $C_{38}H_{46}N_2O_4S_2^{2+}$(658.9) m/$z_{found}$=329.

Example A25

4-[(E)-2-(2,4,6-trimethoxyphenyl)vinyl]-1-[2-[2-[4-[(E)-2-(2,4,6-trimethoxyphenyl)vinyl]pyridine-1-ium-1-yl]ethyldisulfanyl]ethyl]pyridine-1-ium-; methanesulfonate (125)

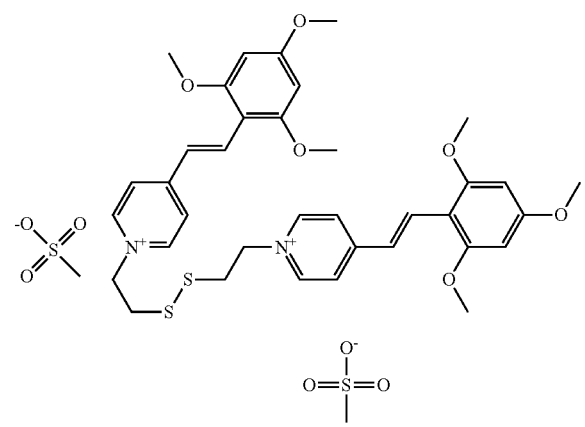

A reaction mixture of 1.5 g (3.0 mmol) of intermediate 3b prepared in example 24b in 50 ml methanol is stirred at 0° C. Then, 1.7 ml (21 mmol) pyrrolidine, 1.3 ml (22.4 mmol) glacial acetic acid and 1.76 g (9.0 mmol) of 2,4,6-trimethoxy benzaldehyde is added. The reaction mixture is reacted and worked-up as described in example A24.

Yield: 510 mg, orange-yellow solid.
$UV_{vis}$: $\lambda_{max}$=418 nm.
$^1$H NMR (DMSO-d$_6$): δ=2.4 (m; CH$_3$S), 3.0 and 3.4 (m; C$\underline{H}_2$), 3.8 and 3.9 (each s; OCH$_3$), 4.75 (m; NCH$_2$), 6.3 (s; Aryl-H); 7.5 and 8.00 (each d; C$\underline{H}$=C$\underline{H}$), 8.1 and 8.75 (each d; Aryl-H) ppm.
MS (ESI) $C_{36}H_{42}N_2O_6S_2^{2+}$(662.86), m/$z_{found}$=331.

B. Application Examples

In the following application examples compositions within the below given definitions are used:
Solution 1 (Permanent Lotion, pH 8.2):
Aqua, Ammonium Thioglycolate, Ammonium Bicarbonate, Ethoxydiglycol, Hexylene Glycol, Thioglycolic Acid; Thiolactic Acid, PEG-60 Hydrogenated Castor Oil, Glycine, Etidronic Acid, Isoceteth-20, Polysilicone-9, Styrene/PVP Copolymer, Trideceth-12, Amodimethicone, Cetrimonium Chloride, Ammonium Hydroxide, Polyquaternium-6, Isopropyl Alcohol, Alcohol denat., Simethicone, Perfume
Solution 2 (Permanent Fixation, pH 3.9):
Based on:
Aqua, Hydrogen Peroxide, Propylene Glycol, Lauryldimonium Hydroxypropyl Hydrolyzed Wheat Protein, PEG-5 Cocamide, Sodium Cocoamphoacetate, Polyquaternium-35, Coco-Betaine, Acetaminophen, Phosphoric Acid, Sodium Chloride, Perfume.

The washing fastness of the dyed hair is analyzed by the Grey scale according to Industrial organic pigments by Herbst&Hunger, 2nd ed. engl. S. 61) Nr 10: DIN 54 001-8-1982, "Herstellung und Bewertung der Aenderung der Farbe", ISO 105-A02-1993.

Example B1 a) 0.5 (abs.) of the dye example A10 is dissolved in water adjusted to pH 9.5 using sodium hydroxide.

This yellow-orange dyeing solution is applied on the dry hair (two blond hair strands) and allowed to stand for 20 min. at 20° C. Then, the strands are rinsed under tap water and dried 12 hours.

b) Solution 1 (permanent lotion) is applied on shampooed hair (two blond hair strands) and allowed to stand for 10 min. Then, the strands are rinsed under tap water, and the towel dry strands are treated with the 0.5%, by weight colouring material solution of example 21a) allowed to stand for 20 min and then rinsed. Then, the towel dry strands are treated with the solution 2 (permanent fixation) and allowed to stand for 10 min. Then the strands are rinsed under tap water and dried 12 hours at.

Example B2 a) 0.5% (abs.) of the dye example A9 is dissolved in water adjusted to pH 9.5 using monoethanolamine.

b) Solution 1 (permanent lotion) is applied on shampooed hair (two blond hair strands) and allowed to stand for 10 min. Then, the strands are rinsed under tap water, and the towel dry strands are treated with the 0.5%, by weight colouring material solution of example 22 a allowed to stand for 20 min and then rinsed. Then, the towel dry strands are treated with the solution 2 (permanent fixation) and allowed to stand for 10 min. Then the strands are rinsed under tap water and dried 12 hours at 20° C.

| Assay | hair type | color | intensity | brilliance | dE* washing fastness 10x washed with shampoo | comment |
|---|---|---|---|---|---|---|
| 1 | blond | yellow-orange | good | good | 11.4 | Example 1a Grey scale: 3 |
|  | blond | yellow-orange | good | good | 4.9 | Example 1b Grey scale: 5 |
| 2 | blond | yellow | good | good | 3.8 | Example 2b Grey scale: 5 |
|  | gray 90% | yellow | good | good | 5.7 | Example 2b Grey scale: 5 |

General Dyeing Procedure:

Solution 1 (permanent lotion) is applied on shampooed hair and allowed to stand for 10 min. Then, the strands are rinsed under tap water, and the towel dry strands are treated with the 0.5% (abs.), by weight coloring material solution (adjusted to pH 9.5 using sodium hydroxide or mono ethanolamine) allowed to stand for 20 min and then rinsed. Then, the towel dry strands are treated with the solution 2 (permanent fixation) and allowed to stand for 10 min. Then the strands are rinsed under tap water and dried 12 hours at 20° C.

After the dyeing the hair tresses are washed and rinsed 10 times with a commercial available to color shampoo (Goldwell) and dried 12 hours at 20'C.

The application results according to the general procedure of the synthesized compounds are given in the following table.

| Examples | hair type | color | intensity | brilliance | dE* washing fastness 10x washed with shampoo | Comment: Color material solution |
|---|---|---|---|---|---|---|
| Compound (101) | blond | yellow | good | good | 2.5 | Solution in water at pH 9.5 |
| Compound (101) | brown | yellow | not good | good | 1.4 | Solution in water at pH 9.5 |
| Compound (101) | gray | yellow | good | good | 1.5 | Solution in water at pH 9.5 |
| Compound (101) | asian | yellow | not good | good | 0.5 | Solution in water at pH 9.5 |
| Compound (101) | blond | yellow | good | good | 5.9 | Solution in water at pH 9.5; Without solution 1 and 2 |
| Compound (101) | brown | yellow | not good | good | 1.1 | Solution in water at pH 9.5, Without solution 1 and 2 |
| Compound (101) | gray | yellow | good | good | 7.3 | Solution in water at pH 9.5, Without solution 1 and 2 |
| Compound (101) | asian | yellow | not good | good | 0.9 | Solution in water at pH 9.5, Without solution 1 and 2 |
| Compound (102) | blond | orange | good | good | 4.2 | Solution in water at pH 9.5 |
| Compound (102) | brown | orange | good | good | 1.1 | Solution in water at pH 9.5 |
| Compound (102) | gray | orange | good | good | 4.1 | Solution in water at pH 9.5 |
| Compound (102) | asian | orange | good | good | 1.3 | Solution in water at pH 9.5 |
| Compound (102) | middle blond | orange | good | good | 1.8 | Solution in water at pH 9.5 |
| Compound (102) | blond | orange | good | good | 9.2 | Solution in water at pH 9.5, Without solution 1 and 2 |
| Compound (102) | brown | orange | good | good | 2.2 | Solution in water at pH 9.5; Without solution 1 and 2 |
| Compound (103) | blond | yellow | good | good | 1.1 | Solution in water at pH 9.5 |
| Compound (103) | brown | yellow | not good | good | 1.5 | Solution in water at pH 9.5 |
| Compound (103) | gray | yellow | good | good | 2.7 | Solution in water at pH 9.5 |
| Compound (103) | asian | yellow | not good | good | 0.5 | Solution in water at pH 9.5 |
| Compound (103) | middle blond | yellow | good | good | 4.5 | Solution in water at pH 9.5 |

-continued

| Examples | hair type | color | intensity | brilliance | dE* washing fastness 10x washed with shampoo | Comment: Color material solution |
|---|---|---|---|---|---|---|
| Compound (103) | blond | yellow | good | good | 5.8 | Solution in water at pH 9.5, Without solution 1 and 2 |
| Compound (103) | middle blond | yellow | good | good | 3.2 | Solution in water at pH 9.5; Without solution 1 and 2 |
| Compound (104) | blond | yellow | good | good | 2.24 | Solution in water at pH 9.5 |
| Compound (104) | brown | yellow | good | good | 0.55 | Solution in water at pH 9.5 |
| Compound (104) | gray | yellow | good | good | 2.51 | Solution in water at pH 9.5 |
| Compound (104) | asian | yellow | good | good | 0.44 | Solution in water at pH 9.5 |
| Compound (105) | blond | yellow | good | good | 3.1 | Solution in water at pH 9.5 |
| Compound (105) | brown | yellow | good | good | 0.9 | Solution in water at pH 9.5 |
| Compound (105) | gray | yellow | good | good | 1.9 | Solution in water at pH 9.5 |
| Compound (105) | asian | yellow | good | good | 0.8 | Solution in water at pH 9.5 |
| Compound (106) | blond | yellow | good | good | 3.2 | Solution in water at pH 9.5 |
| Compound (106) | brown | yellow | good | good | 1.4 | Solution in water at pH 9.5 |
| Compound (106) | gray | yellow | good | good | 1.5 | Solution in water at pH 9.5 |
| Compound (106) | asian | yellow | good | good | 0.3 | Solution in water at pH 9.5 |
| Compound (107) | blond | yellow | good | good | 2.01 | Solution in water at pH 9.5 |
| Compound (107) | brown | yellow | good | good | 1.31 | Solution in water at pH 9.5 |
| Compound (107) | gray | yellow | good | good | 4.49 | Solution in water at pH 9.5 |
| Compound (107) | asian | yellow | good | good | 0.28 | Solution in water at pH 9.5 |
| Compound (108) | blond | yellow | good | good | 4.2 | Solution in water at pH 9.5 |
| Compound (108) | brown | yellow | good | good | 0.8 | Solution in water at pH 9.5 |
| Compound (108) | gray | yellow | good | good | 1.4 | Solution in water at pH 9.5 |
| Compound (108) | asian | yellow | good | good | 0.5 | Solution in water at pH 9.5 |
| Compound (109) | blond | yellow | good | good | 3.8 | Solution in water at pH 9.5; Grey scale: 5 |
| Compound (109) | gray | yellow | good | good | 5.7 | Solution in water at pH 9.5; Grey scale: 5 |
| Compound (110) | blond | yellow-orange | good | good | 4.9 | Solution in water at pH 9.5; Grey scale: 5 |
| Compound (110) | blond | yellow-orange | good | good | 11.4 | Solution in water at pH 9.5, Without solution 1 and 2; Grey scale: 3 |
| Compound (111) | blond | yellow | good | good | 2.16 | Solution in water at pH 9.5 |
| Compound (111) | brown | yellow | not good | good | 0.62 | Solution in water at pH 9.5 |
| Compound (111) | gray | yellow | good | good | 2.88 | Solution in water at pH 9.5 |
| Compound (111) | asian | yellow | not good | good | 0.94 | Solution in water at pH 9.5 |
| Compound (113) | blond | yellow | good | good | 2.95 | Solution in water at pH 9.5 |

-continued

| Examples | hair type | color | intensity | brilliance | dE* washing fastness 10x washed with shampoo | Comment: Color material solution |
|---|---|---|---|---|---|---|
| Compound (113) | brown | yellow | not good | good | 2.05 | Solution in water at pH 9.5 |
| Compound (113) | gray | yellow | good | good | 3.09 | Solution in water at pH 9.5 |
| Compound (113) | asian | yellow | not good | good | 0.36 | Solution in water at pH 9.5 |
| Compound (114) | blond | yellow | good | good | 2.7 | Solution in water at pH 9.5 |
| Compound (114) | brown | yellow- | not good | good | 0.5 | Solution in water at pH 9.5 |
| Compound (114) | gray | yellow | good | good | 4.0 | Solution in water at pH 9.5 |
| Compound (114) | asian | yellow | not good | good | 0.6 | Solution in water at pH 9.5 |
| Compound (114) | blond | yellow | good | good | 12.8 | Solution in water at pH 9.5; Without solution 1 and 2 |
| Compound (114) | brown | yellow | not good | good | 0.6 | Solution in water at pH 9.5, Without solution 1 and 2 |
| Compound (114) | gray | yellow | good | good | 12.8 | Solution in water at pH 9.5, Without solution 1 and 2 |
| Compound (114) | asian | yellow | not good | good | 1.0 | Solution in water at pH 9.5, Without solution 1 and 2 |
| Compound (115) | blond | yellow | good | good | 1.78 | Solution in water at pH 9.5 |
| Compound (115) | brown | yellow | good | good | 0.33 | Solution in water at pH 9.5 |
| Compound (115) | gray | yellow | good | good | 2.37 | Solution in water at pH 9.5 |
| Compound (115) | asian | yellow | good | good | 0.1 | Solution in water at pH 9.5 |
| Compound (116) | blond | yellow | good | good | 2.6 | Solution in water at pH 9.5 |
| Compound (116) | brown | yellow | not good | good | 1.17 | Solution in water at pH 9.5 |
| Compound (116) | gray | yellow | good | good | 4.94 | Solution in water at pH 9.5 |
| Compound (116) | asian | yellow | not good | good | 0.19 | Solution in water at pH 9.5 |
| Compound (117) | blond | yellow | good | good | 5.6 | Solution in water at pH 9.5 |
| Compound (117) | blond | yellow- | good | good | 27.0 | Solution in water at pH 9.5; Without solution 1 and 2 |
| Compound (118) | blond | yellow | good | good | 2.1 | Solution in water at pH 9.5 |
| Compound (118) | brown | yellow | not good | good | 1.3 | Solution in water at pH 9.5 |
| Compound (118) | gray | yellow | good | good | 4.0 | Solution in water at pH 9.5 |
| Compound (118) | asian | yellow | not good | good | 1.5 | Solution in water at pH 9.5 |
| Compound (118) | Middle-blond | yellow | good | good | 3.2 | Solution in water at pH 9.5 |
| Compound (118) | blond | yellow | good | good | 9.0 | Solution in water at pH 9.5. Without solution 1 and 2 |
| Compound (118) | brown | yellow | not good | good | 0.7 | Solution in water at pH 9.5. Without solution 1 and 2 |
| Compound (119) | blond | yellow | not good | good | 0.8 | Solution in water at pH 9.5 |
| Compound (119) | brown | yellow- | not good | good | 1.1 | Solution in water at pH 9.5 |

-continued

| Examples | hair type | color | intensity | brilliance | dE* washing fastness 10x washed with shampoo | Comment: Color material solution |
|---|---|---|---|---|---|---|
| Compound (119) | gray | yellow | not good | good | 3.5 | Solution in water at pH 9.5 |
| Compound (119) | asian | yellow | not good | good | 0.5 | Solution in water at pH 9.5 |
| Compound (119) | middle blond | yellow | not good | good | 2.2 | Solution in water at pH 9.5 |
| Compound (120) | blond | orange | good | good | 2.8 | Solution in water at pH 9.5 |
| Compound (120) | brown | orange | good | good | 0.6 | Solution in water at pH 9.5 |
| Compound (120) | gray | orange | good | good | 6.6 | Solution in water at pH 9.5 |
| Compound (120) | asian | orange | good | good | 0.8 | Solution in water at pH 9.5 |
| Compound (120) | middle blond | orange | good | good | 7.4 | Solution in water at pH 9.5 |
| Compound (120) | blond | orange | good | good | 7.4 | Solution in water at pH 9.5; Without solution 1 and 2 |
| Compound (120) | brown | orange | not good | good | 0.9 | Solution in water at pH 9.5; Without solution 1 and 2 |
| Compound (121) | blond | yellow | good | good | 3.8 | Solution in water at pH 9.5 |
| Compound (121) | brown | yellow | not good | good | 0.7 | Solution in water at pH 9.5 |
| Compound (121) | gray | yellow | good | good | 3.5 | Solution in water at pH 9.5 |
| Compound (121) | asian | yellow | not good | good | 0.5 | Solution in water at pH 9.5 |
| Compound (121) | middle blond | yellow | good | good | 9.6 | Solution in water at pH 9.5 |
| Compound (121) | blond | yellow | good | good | 8.2 | Solution in water at pH 9.5; Without solution 1 and 2 |
| Compound (121) | brown | yellow | not good | good | 1.9 | Solution in water at pH 9.5; Without solution 1 and 2 |
| Compound (124) | blond | yellow | good | good | 5.0 | Solution in water at pH 9.5 |
| Compound (124) | blond | yellow | good | good | 13.1 | Solution in water at pH 9.5; Without solution 1 and 2 |
| Compound (125) | blond | yellow | good | good | 2.5 | Solution in water at pH 9.5 |
| Compound (125) | blond | yellow | good | good | 16.1 | Solution in water at pH 9.5; Without solution 1 and 2 |

The invention claimed is:
1. A styryl sulfide dye of formula (110)
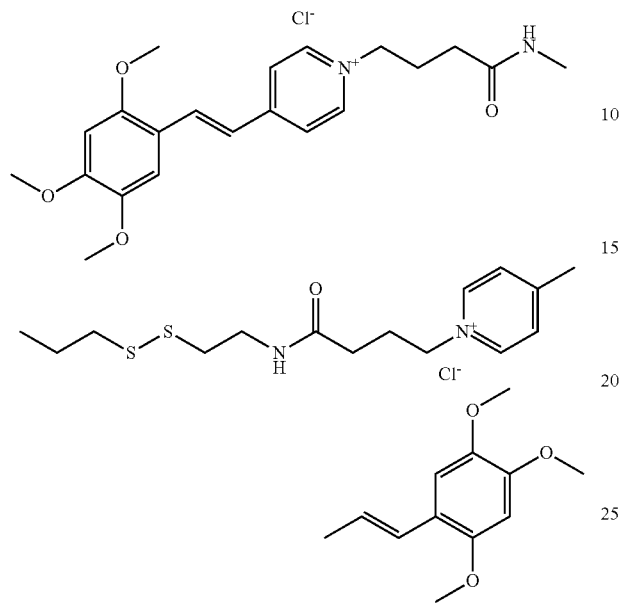
Formula (110).